United States Patent
Reddy et al.

(10) Patent No.: US 11,781,070 B2
(45) Date of Patent: Oct. 10, 2023

(54) MESOGEN COMPOUNDS

(71) Applicant: Transitions Optical, Ltd., Tuam (IE)

(72) Inventors: Ramaiahgari Reddy, Murrysville, PA (US); Yannian Li, Murrysville, PA (US); Alan M. Grubb, Pittsburgh, PA (US)

(73) Assignee: Transitions Optical, Ltd., Tuam (IE)

( * ) Notice: Subject to any disclaimer, the term of this patent is extended or adjusted under 35 U.S.C. 154(b) by 0 days.

(21) Appl. No.: 17/631,007

(22) PCT Filed: Jul. 30, 2019

(86) PCT No.: PCT/EP2019/070442
§ 371 (c)(1),
(2) Date: Jan. 28, 2022

(87) PCT Pub. No.: WO2021/018383
PCT Pub. Date: Feb. 4, 2021

(65) Prior Publication Data
US 2022/0275278 A1 Sep. 1, 2022

(51) Int. Cl.
*G02F 1/1333* (2006.01)
*C09K 19/46* (2006.01)
*C07C 69/92* (2006.01)
*C09K 19/38* (2006.01)
*C09K 19/56* (2006.01)
*C09K 19/60* (2006.01)
*G02F 1/1337* (2006.01)
*C09K 19/04* (2006.01)

(52) U.S. Cl.
CPC ............. *C09K 19/46* (2013.01); *C07C 69/92* (2013.01); *C09K 19/3857* (2013.01); *C09K 19/56* (2013.01); *C09K 19/60* (2013.01); *G02F 1/1337* (2013.01); *C09K 2019/0448* (2013.01)

(58) Field of Classification Search
CPC ........ C09K 19/04; C09K 19/46; C09K 19/56; C09K 19/60; C09K 19/38; C09K 19/3804; C09K 19/3857; C09K 2019/0444; C09K 2019/0448; G02F 1/1333; G02F 1/1337; C07C 69/92
See application file for complete search history.

(56) References Cited

U.S. PATENT DOCUMENTS

| | | | |
|---|---|---|---|
| 7,910,019 B2 | 3/2011 | He et al. | |
| 7,910,020 B2 | 3/2011 | He et al. | |
| 8,349,210 B2 | 1/2013 | Xu et al. | |
| 8,409,674 B2 | 4/2013 | Harding et al. | |
| 8,628,685 B2 | 1/2014 | He et al. | |
| 8,828,284 B2 | 9/2014 | Carpenter | |
| 8,926,091 B2 | 1/2015 | Kumar et al. | |
| 9,334,439 B2 | 5/2016 | DeMeio et al. | |
| 9,683,102 B2 | 6/2017 | Cefalo et al. | |
| 2012/0002141 A1 | 1/2012 | Dai et al. | |
| 2015/0234208 A1 | 8/2015 | De Ayguavives et al. | |
| 2017/0275534 A1 | 9/2017 | Reddy et al. | |
| 2022/0049161 A1* | 2/2022 | Reddy | C09K 19/3001 |
| 2022/0275278 A1* | 9/2022 | Reddy | C07C 69/92 |

FOREIGN PATENT DOCUMENTS

| | | |
|---|---|---|
| DE | 19941567 A1 | 4/2000 |
| EP | 1412447 B1 | 9/2008 |
| JP | 2000111922 A | 4/2000 |
| JP | 200475623 A | 3/2004 |
| JP | 2006265403 A | 10/2006 |
| WO | 2009158483 A1 | 12/2009 |
| WO | 2009158488 A1 | 12/2009 |

OTHER PUBLICATIONS

Mandle et al., "Developments in liquid-crystalline dimers and oligomers", Liquid Crystals, 2017, pp. 2046-2059, vol. 44:12-13.
Nakanishi et al. , "Synthesis of Novel Glass-Forming Liquid Crystals Containing Acrylic Acid Trimer Core Unit and Mesogenic Moiety, and Their Use in Cholesteric Reflection Films", Polymer Journal, 2007, pp. 252-258, vol. 39:3.
Tsuji et al., "Chiral Liquid Crystal Trimer Exhibiting an Optically Uniaxial Smectic Phase with a Double-Peak Polarization", 2012, J. Phys. Chem. C, pp. 8678-8687, vol. 116.
Wiegand et al., "aSynthesis and Characterization of Triptycene-Based Polyimides with Tunable High Fractional Free Volume for Gas Separation Membranes," 2014, Journal of Material Chemistry A, pp. 1-29, vol. 2:33.

\* cited by examiner

*Primary Examiner* — Geraldina Visconti
(74) *Attorney, Agent, or Firm* — THE WEBB LAW FIRM

(57) ABSTRACT

The present invention relates to mesogen compounds that include first, second, and third mesogens, in which the first and second mesogens are connected by a first linking group ($-L^1-$), and the second and third mesogens are connected by a second linking group ($-L^2-$), as represented by the following Formula (I), and as graphically illustrated by Formula (Ia) of FIG. 1 of the drawing:

(Mesogen-1)-$L^1$-(Mesogen-2)-$L^2$-(Mesogen-3)    (I)

At least one of Mesogen-1, Mesogen-2, or Mesogen-3 include at least four cyclic groups. The linking groups -$L^1$- and -$L^2$- are each free of mesogen properties (are each non-mesogenic) and each independently have an average chain length of at least 20 bonds. The mesogen compounds are optionally polymerizable. The present invention also relates to liquid crystal compositions that include such mesogen compounds, and to optical elements that include such mesogen compounds, such as in one or more mesogen-containing layers.

15 Claims, 1 Drawing Sheet

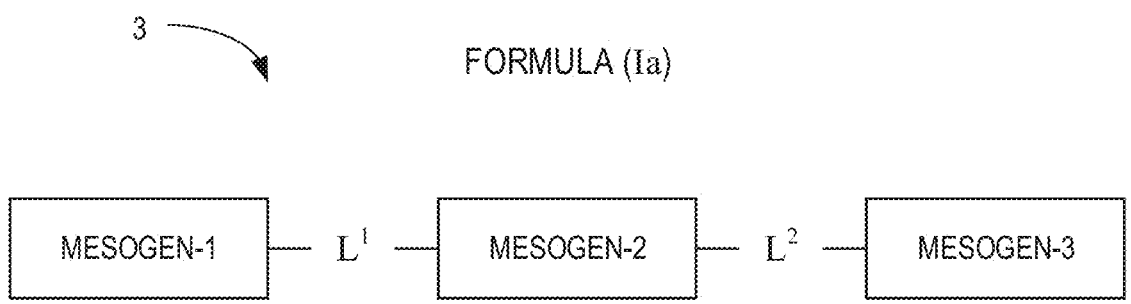
FORMULA (Ia)

MESOGEN COMPOUNDS

CROSS-REFERENCE TO RELATED APPLICATION

This application is the United States national phase of International Application No. PCT/EP2019/070442 filed Jul. 30, 2019, the disclosure of which is hereby incorporated by reference in its entirety.

FIELD

The present invention relates to mesogen compounds that include first, second, and third mesogens, in which the first and second mesogens are connected by a first linking group, and the second and third mesogens are connected by a second linking group, and which are optionally polymerizable, to liquid crystal compositions that include such mesogen compounds, and to optical elements that include such mesogen compounds.

BACKGROUND

The molecules of a liquid crystal are typically capable of aligning with one another in substantially one direction, which results in a fluid material having anisotropic properties, such as with regard to optical, electromagnetic, and/or mechanical properties. A mesogen is typically described as the primary or fundamental unit (or segment or group) of a liquid crystal material that induces, and/or is induced into, structural order amongst and between liquid crystals (such as, other liquid crystal materials that are present).

Liquid crystal polymers are polymers capable of forming regions of highly ordered structure while in a liquid phase. Liquid crystal polymers have a wide range of uses, including engineering plastics, and gels for liquid crystal displays (LCD's). The structure of liquid crystal polymers can be described as being composed of densely packed elongated polymer chains that provide self-reinforcement almost to the melting point of the polymer.

Dichroism can occur in liquid crystals, including mesogen compounds, due to the optical anisotropy of the molecular structure, or the presence of impurities, or the presence of dichroic dyes and/or photochromic-dichroic materials. As used herein, the term "dichroism" and similar terms, such as "dichroic" means the ability to absorb one of two orthogonal plane polarized components of radiation (including transmitted and/or reflected radiation) more strongly than the other orthogonal plane polarized component. Photochromic-dichroic materials possess both photochromic properties and dichroic properties. A photochromic-dichroic material, in some instances, can be described as including a photochromic molecule (or core, or moiety) to which is covalently attached at least one lengthening group at least a portion of which is capable of being aligned with (or by) a mesogenic material.

When used in combination with liquid crystal materials, such as mesogen compounds, the dichroic properties of photochromic-dichroic compounds, such as polarization efficiency and absorption ratio, can be enhanced. While not intending to be bound by any theory, it is believed based on the evidence at hand, that alignment of the photochromic-dichroic compounds with aligned mesogen compounds enhances the dichroic properties of the photochromic-dichroic compounds, such as improved absorption ratio (AR) values.

The photochromic properties of photochromic-dichroic compounds can be enhanced by a chemical environment that allows the photochromic portion thereof to efficiently undergo a reversible conformational change between an absorbing (or colored state) and a non-absorbing (or non-colored state). Examples of quantifiable photochromic properties include, but are not limited to: fade rate (sometimes referred to as fade half-life, $T_{1/2}$); change in optical density (sometimes designated as $\Delta OD$); the change in optical density ($\Delta OD$) at saturation; sensitivity (sometimes designated as $\Delta OD/Min$); and the efficiency at which the photochromic compound absorbs radiation required to activate the photochromic compound (sometimes designated as chromaticity). The chemical environment provided by the aligned mesogen compounds, while enhancing dichroic properties of the dichroic portion of a photochromic-dichroic compound, can in some instances provide a chemical environment that adversely restricts or limits the efficient reversible conformational change of the photochromic portion of the photochromic-dichroic compound.

It would be desirable to develop new mesogen compounds that are capable of further enhancing the dichroic properties of dichroic materials, such as photochromic-dichroic compounds. It would be further desirable that such newly developed mesogen compounds maintain or enhance the photochromic properties of photochromic-dichroic materials used in conjunction therewith.

SUMMARY

In accordance with the present invention, there is provided a mesogen-containing compound represented by the following Formula (I), and as graphically illustrated by Formula (Ia) of FIG. 1 of the drawing, $$(\text{Mesogen-1})\text{-L}^1\text{-}(\text{Mesogen-2})\text{-L}^2\text{-}(\text{Mesogen-3}) \qquad (I)$$

With reference to Formula (I), (A) Mesogen-1 and Mesogen-3 are each independently represented by the following Formula (II),

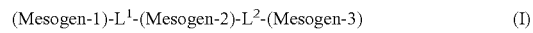

$$P\text{—}(S_1)_d\text{—}Q_1\text{—}(S_2)_e\text{—}Q_2\text{—}_{e'}\text{—}(S_3)_f\text{—}Q_3\text{—}_{f'}\text{—}(S_4)_g\text{—} \qquad (II)$$

With reference to Formula (II), P is selected from hydrogen, halogen, alkyl, haloalkyl, alkoxy, haloalkoxy, acrylate, methacrylate, trihalomethacrylate, cyanoacrylate, acrylamido, methacrylamido, oxirane, hydroxyl, primary amino, carboxylic acid, or carboxylic acid ester.

With further reference to Formula (I), (B) Mesogen-2 is represented by the following Formula (III),

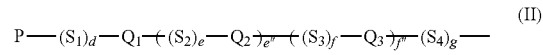

$$\text{—}(S_1)_d\text{—}Q_1\text{—}(S_2)_e\text{—}Q_2\text{—}_{e'}\text{—}(S_3)_f\text{—}Q_3\text{—}_{f'}\text{—}(S_4)_g\text{—} \qquad (III)$$

Independently for each of Formula (II) and Formula (III):
$S_1$, $S_2$, $S_3$, and $S_4$, for each occurrence, are independently selected from a spacer unit chosen from: —$CH_2$—; —O—; —C(O)—; —N=N—; —CH=CH—; —C≡C—; —CH=N—; —$CF_2$—; or —NH—, provided that when two spacer units comprising heteroatoms are linked together the spacer units are linked so that heteroatoms are not directly linked to each other;

d is 0 to 20;

e, f, and g, for each occurrence, are independently 0 to 3;

$Q_1$, $Q_2$, and $Q_3$, for each occurrence, are independently a divalent group selected from the group consisting of: unsubstituted or substituted cycloaliphatic group; unsubstituted or substituted heterocycloaliphatic group; unsubstituted or substituted aryl; and unsubstituted or substituted heteroaryl; wherein the cycloaliphatic group substituents, heterocycloaliphatic group substituents, aryl substituents, and heteroaryl substituents are each independently selected from cyano or $-(S_1)_d-P$, where $S_1$, d, and P are each as defined with regard to Formula (II); and e'' and f'', for each occurrence, are independently from 0 to 6, provided the sum of e'' and f'' is at least 1.

With additional reference to Formula (I), (C) $-L^1-$ and $-L^2-$ are each independently represented by the following Formula (IV), $$-(A-B)_y-E- \qquad (IV)$$

With reference to Formula (IV):

(i) y is 0 to 30;

(ii) each A independently for each y is a divalent group selected from the group consisting of aliphatic group and haloaliphatic group;

(iii) each B independently for each y is a divalent group selected from the group consisting of: —O—; —C(O)O—; —OC(O)O—; —C(O)N($R_1$)— where $R_1$ is H or alkyl;

—NH—C(O)O—; —N($R_2$)C(O)N($R_2$)— where each $R_2$ is independently selected from H or alkyl;

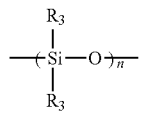

where n is 1 to 5, and each $R_3$ independently for each n is selected from methyl, ethyl, or phenyl; and —Si($R_4$)($R_4$)— where each $R_4$ is independently selected from methyl, ethyl, or phenyl; and (iv) E is a divalent group selected from the group consisting of aliphatic group and haloaliphatic group.

With reference to Formula (I), it is provided that:

at least one of Mesogen-1, Mesogen-2, or Mesogen-3 include at least four cyclic groups; and $-L^1-$ and $-L^2-$ each independently comprise an average chain length of at least 20 bonds.

In further accordance with the present invention, there is provided liquid crystal compositions that include the mesogen-containing compound of the present invention, such as described with reference to Formula (I).

There is provided, in further accordance with the present invention, an optical element that comprises: a substrate; and a layer on at least a portion of a surface of the substrate, in which the layer comprises the mesogen-containing compound of the present invention, such as described with reference to Formula (I).

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWING

FIG. 1 is a representative graphical illustration, designated as Formula (Ia), of a mesogen-containing compound (3) of the present invention.

DETAILED DESCRIPTION

The mesogen compounds of the present invention, such as represented by Formula (I), are referred to herein as "mesogen compounds", "mesogen-containing compounds", "trimesogens", and "trimesogen compounds".

As used herein, the articles "a", "an", and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

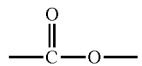

or equivalently —C(O)O—, is inclusive of the right-to-left representation thereof,

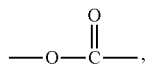

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about".

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, "at least one of" is synonymous with "one or more of", whether the elements are listed conjunctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from" whether the elements are listed conjunctively or disjunctively. Further, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the invention herein may describe certain features as being "particularly" or "preferably" within certain limitations (e.g., "preferably", "more preferably", or "even more preferably", within certain limitations). It is to be understood that the invention is not limited to or by these particular or preferred limitations, but encompasses the entire scope of the disclosure.

As used herein, the term "(meth)acrylate" and similar terms, such as "(meth)acrylic acid ester", means methacrylates and/or acrylates. As used herein, and in accordance with some embodiments, the term "(meth)acrylate" such as with regard to groups, and substituents of various groups, of the mesogen compounds of the present invention, and related terms, such as "(meth)acrylate group" and "(meth)acrylate substituent", includes a material represented by —O—C(O)—C(R')=CH$_2$, where R' is hydrogen or methyl. As used herein, the term "(meth)acrylic acid" means methacrylic acid and/or acrylic acid.

As used herein, the term "(meth)acrylamido" means acrylamido (—N(H)—C(O)—C(H)=CH$_2$) and methacrylamido (—N(H)—C(O)—C(CH$_3$)=CH$_2$).

As used herein, and in accordance with some embodiments, the term "carboxylic acid" such as with regard to groups, and substituents of various groups, of the mesogen-containing compounds of the present invention, and related terms, such as "carboxylic acid group" and "carboxylic acid substituent" includes a material represented by —C(O)OH.

As used herein, and in accordance with some embodiments, the term "carboxylic acid ester" such as with regard to groups, and substituents of various groups, of the mesogen-containing compounds of the present invention, and related terms, such as "carboxylic acid ester group" and "carboxylic acid ester substituent", means a material represented by —C(O)OR, where R is, for example, selected from unsubstituted and substituted aliphatic groups, unsubstituted and substituted cyclo aliphatic groups, unsubstituted and substituted heterocycloaliphatic groups, unsubstituted and substituted aryl, and unsubstituted and substituted hetero aryl.

As used herein, the term "photochromic" and similar terms, such as "photochromic compound", means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as discussed in further detail herein.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state (such as a "clear state") to a second state (such as a "colored state") in response to actinic radiation, and reverting back to the first state in response to thermal energy. The term "non-thermally reversible photochromic compounds/materials" as used herein means compounds/materials capable of converting from a first state (such as a "clear state") to a second state (such as a "colored state") in response to actinic radiation, and reverting back to the first state in response to actinic radiation of substantially the same wavelength(s) as the absorption(s) of the colored state.

As used herein, to modify the term "state", the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds used in conjunction with the present invention can have a different absorption spectrum in each of the first and second state. For example, while not limiting herein, a photochromic compound used in conjunction with the present invention can be clear in the first state and colored in the second state. Alternatively, a photochromic compound used in conjunction with the present invention can have a first color in the first state and a second color in the second state. Additionally, a photochromic-dichroic compound used in conjunction with the present invention can have a first alignment in a first state, and a second alignment in a second state, in which one of the first alignment and second alignment is substantially non-aligned.

As used herein, the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein, the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation contact lenses, intra-ocular lenses, magnifying lenses, and protective lenses or visors.

As used herein, the term "display" means the visible or machine-readable representation of information in words, numbers, symbols, designs or drawings. Non-limiting examples of display elements include screens, monitors, and security elements, such as security marks.

As used herein, the term "window" means an aperture adapted to permit the transmission of radiation there-through. Non-limiting examples of windows include automotive and aircraft transparencies, windshields, filters, shutters, and optical switches.

As used herein, the term "mirror" means a surface that specularly reflects a large fraction of incident light.

As used herein, the term "liquid crystal cell" refers to a structure containing a liquid crystal material that is capable of being ordered. A non-limiting example of a liquid crystal cell element is a liquid crystal display.

As used herein, spatial or directional terms, such as "left", "right", "inner", "outer", "above", "below", and the like, relate to the invention as it is depicted. It is to be understood, however, that the invention can assume various alternative orientations and, accordingly, such terms are not to be considered as limiting.

As used herein, the terms "formed over", "deposited over", "provided over", "applied over", residing over", or "positioned over", mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

All documents, such as but not limited to issued patents and patent applications, referred to herein, and unless otherwise indicated, are to be considered to be "incorporated by reference" in their entirety.

As used herein, the term "aliphatic" and related terms, such as "aliphatic group(s)", means non-cyclic and non-aromatic hydrocarbon groups, which include at least one carbon atom, such as 1 to 20 carbon atoms, such as $C_1$-$C_{20}$ aliphatic groups, or $C_1$-$C_{10}$ aliphatic groups, or $C_1$-$C_6$ aliphatic groups; can be linear or branched; optionally include one or more interior and/or terminal alkene (or alkenyl) groups; and optionally included one or more interior and/or terminal alkyne (or alkynyl) groups. When including two or more alkene groups, the alkene groups of an aliphatic group can be conjugated and/or non-conjugated. When including two or more alkyne groups, the alkyne groups of an aliphatic group can be conjugated and/or non-conjugated. When including at least one alkene group and at least one alkyne group, the alkene and alkyne groups of the aliphatic group can be conjugated and/or non-conjugated relative to each other.

Examples of aliphatic groups include, but are not limited to, alkyl groups. As used herein, the term "alkyl" and related terms, such as "alkyl group(s)", means groups which include at least one carbon atom, such as 1 to 20 carbon atoms, such as $C_1$-$C_{20}$ alkyl groups, or $C_1$-$C_{10}$ alkyl groups, or $C_1$-$C_6$ alkyl groups; are linear or branched; and are saturated (and correspondingly are free of alkene groups and alkyne groups). Examples of alkyl groups include, but are not limited to, methyl, ethyl, n-propyl, iso-propyl, n-butyl, iso-butyl, sec-butyl, t-butyl, linear or branched pentyl, linear or branched hexyl, linear or branched heptyl, linear or branched octyl, linear or branched nonyl, linear or branched decyl, linear or branched undencyl, linear or branched dodecyl, linear or branched tridecyl, linear or branched tetradecyl, linear or branched pentadecyl, linear or branched hexadecyl, linear or branched heptadecyl, linear or branched octadecyl, linear or branched nonadecyl, and linear or branched eicosanyl.

As used herein, recitations of "linear or branched" groups, such as, but not limited to, linear or branched alkyl, are herein understood to include, for purposes of non-limiting illustration, a methylene group or a methyl group; groups that are linear, such as linear $C_2$-$C_{20}$ alkyl groups; and groups that are appropriately branched, such as, but not limited to, branched $C_3$-$C_{20}$ alkyl groups.

Examples of aliphatic groups include, but are not limited to, alkenyl groups. As used herein, the term "alkenyl" and related terms, such as "alkenyl groups", means groups which include at least two carbon atoms, such as 2 to 20 carbon atoms, such as $C_2$-$C_{20}$ alkenyl groups, or $C_2$-$C_{10}$ alkenyl groups, or $C_2$-$C_6$ alkenyl groups; are linear or branched; and include one or more interior and/or terminal alkene (or alkenyl) groups. Examples of alkenyl groups include, but are not limited to, those examples of linear or branched alkyl groups recited previously herein, which have at least two carbon atoms and at least one alkene (or alkenyl) group, such as, but not limited to, ethenyl, linear or branched propenyl, linear or branched butenyl, linear or branched pentenyl, linear or branched hexencyl, etc.

Examples of aliphatic groups include, but are not limited to alkynyl groups. As used herein, the term "alkynyl" and related terms, such as "alkynyl group(s)", means groups which include at least two carbon atoms, such as 2 to 20 carbon atoms, such as $C_2$-$C_{20}$ alkynyl groups, or $C_2$-$C_{10}$ alkynyl groups, or $C_2$-$C_6$ alkynyl groups; are linear or branched; and include one or more interior and/or terminal alkyne (or alkynyl) groups. Examples of alkynyl groups include, but are not limited to, those examples of linear or branched alkyl groups recited previously herein, which have at least two carbon atoms and at least one alkyne (or alkynyl) group, such as, but not limited to, ethynyl, propynyl, butynyl, linear or branched pentynyl, linear or branched hexynyl, etc.

As used herein, the term "haloaliphatic" and related terms, such as "haloaliphatic group(s)", means non-cyclic and non-aromatic hydrocarbon groups, which include at least one carbon atom, such as 1 to 20 carbon atoms, such as $C_1$-$C_{20}$ haloaliphatic groups, or $C_1$-$C_{10}$ haloaliphatic groups, or $C_1$-$C_6$ haloaliphatic groups; include at least one halo group selected from fluoro (F), chloro (Cl), bromo (Br), and/or iodo (I); are linear or branched; optionally include one or more interior and/or terminal alkene groups; and optionally include one or more interior and/or terminal alkyne groups. When including two or more alkene groups, the alkene groups of an haloaliphatic group can be conjugated and/or non-conjugated. When including two or more alkyne groups, the alkyne groups of an haloaliphatic group can be conjugated and/or non-conjugated. When including at least one alkene group and at least one alkyne group, the alkene and alkyne groups of the haloaliphatic group can be conjugated and/or non-conjugated relative to each other. At least one available hydrogen of, and up to all available hydrogens of, a haloaliphatic group can be replaced with a halo group, such as selected from fluoro (F), chloro (Cl), bromo (Br), and/or iodo (I). Correspondingly, as used herein, the term "haloaliphatic" includes, but is not limited to, "perhaloaliphatic" and related terms, such as "perhaloaliphatic group(s)".

Examples of haloaliphatic groups include, but are not limited to, haloalkyl groups. As used herein, the term "haloalkyl" and related terms, such as "haloalkyl group(s)", means groups which include at least one carbon atom, such as 1 to 20 carbon atoms, such as $C_1$-$C_{20}$ haloalkyl, or $C_1$-$C_{10}$ haloalkyl, or $C_1$-$C_6$ haloalkyl; are linear or branched; include at least one halo group, such as selected from fluoro (F), chloro (Cl), bromo (Br), and/or iodo (I); and are saturated (and correspondingly are free of alkene groups and alkyne groups). At least one available hydrogen of, and up to all available hydrogens of, a haloalkyl group can be replaced with a halo group, such as selected from fluoro (F), chloro (Cl), bromo (Br), and/or iodo (I). Correspondingly, as used herein, the term "haloalkyl" includes, but is not limited to, "perhaloalkyl" and related terms, such as "perhaloalkyl group(s)". Examples of haloalkyl groups include, but are not limited to, those examples of linear or branched alkyl groups recited above, which include at least one halo group, such as, but not limited to, halomethyl, haloethyl, linear or branched halopropyl, linear or branched halobutyl, linear or branched halopentyl, linear or brached halohexyl, etc., each independently including at least one halo group.

Examples of haloaliphatic groups include, but are not limited to, haloalkenyl groups. As used herein, the term "haloalkenyl" and related terms, such as "haloalkenyl group(s)", means groups which include at least two carbon atoms, such as 2 to 20 carbon atoms, such as $C_2$-$C_{20}$ haloalkenyl, or $C_2$-$C_{10}$ haloalkenyl, or $C_2$-$C_6$ haloalkenyl; are linear or branched; include at least one halo group, such as selected from fluoro (F), chloro (Cl), bromo (Br), and/or iodo (I); and include one or more interior and/or terminal alkene (or alkenyl) groups. Examples of haloalkenyl groups include, but are not limited to, those examples of linear or branched alkyl groups recited above, which have at least two carbon atoms, at least one alkene (or alkenyl) group, and at least one halo group, such as, but not limited to, haloethenyl, linear or branched halopropenyl, linear or branched halobutenyl, linear or branched halopentenyl, linear or branched halohexenyl, etc., each independently including at least one halo group.

Examples of haloaliphatic groups include, but are not limited to, haloalkynyl groups. As used herein, the term "haloalkynyl" and related terms, such as "haloalkynyl group(s)", means groups which include at least two carbon atoms, such as 2 to 20 carbon atoms, such as $C_2$-$C_{20}$ haloalkynyl, or $C_2$-$C_{10}$ haloalkynyl, or $C_2$-$C_6$ haloalkynyl; are linear or branched; include at least one halo group (or halogen group), such as selected from fluoro (F), chloro (Cl), bromo (Br), and/or iodo (I); and include one or more interior and/or terminal alkyne (or alkynyl) groups. Examples of haloalkynyl groups include, but are not limited to, those examples of linear or branched alkyl groups recited above, which have at least two carbon atoms, at least one alkyne (or alkynyl) group, and at least one halo group, such as, but not limited to, haloethynyl, halopropynyl, halobutynyl, linear or branched halopentynyl, linear or branched halohexynyl, etc., each independently including at least one halo group.

As used herein, the term "cycloaliphatic" and related terms, such as "cycloaliphatic group(s)", means cyclic and non-aromatic hydrocarbon groups, which include at least three carbon atoms, such as 3 to 20 carbon atoms, such as $C_3$-$C_{20}$ cycloaliphatic groups, or $C_3$-$C_{10}$ cycloaliphatic groups, or $C_3$-$C_8$ cycloaliphatic groups; optionally include at least one unsaturated group selected from alkene and/or alkyne; and optionally include two or more fused cycloaliphatic rings.

Examples of cycloaliphatic groups include, but are not limited to, cycloalkyl groups. As used herein, the term "cycloalkyl" and related terms, such as "cycloalkyl group(s)", means groups which include at least three carbon atoms, such as 3 to 20 carbon atoms, such as $C_3$-$C_{20}$ cycloalkyl groups, or $C_3$-$C_{10}$ cycloalkyl groups, or $C_3$-$C_8$ cycloalkyl groups; optionally include at least one unsaturated group selected from alkene and/or alkyne; and optionally include two or more fused cycloalkyl rings. Examples of cycloalkyl groups include, but are not limited to, cyclopropyl; cyclobutyl; cyclopentyl; cyclohexyl; cycloheptyl; cyclooctyl; cyclononyl; cyclodecyl; cycloundecyl; cyclododecyl; norbornyl; decahydronaphthalenyl; tetradecahydroanthracenyl; tetradecahydrophenanthrenyl; and dodecahydro-1H-phenalenyl.

As used herein, the term "heterocycloaliphatic" and related terms, such as "heterocycloaliphatic group(s)", means cyclic and non-aromatic groups, which include at least two carbon atoms, such as 2 to 20 carbon atoms, such as $C_2$-$C_{20}$ heterocycloaliphatic groups, or $C_2$-$C_{10}$ heterocycloaliphatic groups, or $C_2$-$C_8$ heterocycloaliphatic groups; and which have at least one hetero atom in the cyclic ring, such as, but not limited to, O, S, N, P, and combinations thereof; optionally include at least one unsaturated group selected from alkene and/or alkyne; and optionally include two or more fused non-aromatic cyclic rings, at least one of which is a fused heterocycloaliphatic ring.

Examples of heterocycloaliphatic groups include, but are not limited to, heterocycloalkyl groups. As used herein, the term "heterocycloalkyl" and related terms, such as "heterocycloalkyl group(s)", means groups which include at least two carbon atoms, such as 2 to 20 carbon atoms, such as $C_2$-$C_{20}$ heterocycloalkyl groups, or $C_2$-$C_{10}$ heterocycloalkyl groups, or $C_2$-$C_8$ heterocycloalkyl groups; and which have at least one hetero atom in the cyclic ring, such as, but not limited to, O, S, N, P, and combinations thereof; optionally include at least one unsaturated group selected from alkene and/or alkyne; and optionally include two or more fused non-aromatic cyclic rings, at least one of which is a fused heterocycloalkyl ring. Examples of heterocycloalkyl groups include, but are not limited to, imidazolyl, tetrahydrofuranyl, tetrahydropyranyl, piperidinyl, piperazinyl, morpholinyl, 7-oxabicyclo[2.2.1]heptanyl, octahydrocyclopenta[b]pyranyl, and octahydro-1H-isochromenyl.

As used herein, the term "aryl" and related terms, such as "aryl group(s)" means cyclic aromatic groups, which include at least 6 carbon atoms, such as $C_6$-$C_{20}$ aryl groups, or $C_6$-$C_{14}$ aryl groups; and optionally include at least two fused rings, at least one of which is a fused aromatic ring. Examples of aryl groups include, but are not limited to, phenyl, naphthalenyl, anthracenyl, phenanthrenyl, 3a[1]H-phenalenyl, triphenylenyl, 9,10-dihydroanthracenyl, 9,10-dihydrophenanthrenyl, and triptycenyl.

As used herein, the term "heteroaryl" and related terms, such as "heteroaryl group(s)", means cyclic aromatic groups, which include at least 3 carbon atoms, such as $C_3$-$C_{20}$ heteroaryl groups, or $C_5$-$C_{14}$ heteroaryl groups; at least one heteroatom in the aromatic ring, such as —O—, —N—, and/or —S—; and optionally include at least two fused rings, at least one of which is a fused heteroaromatic ring. Examples of hetroaryl groups include, but are not limited to, pyrazolyl, imidazolyl, triazinyl, furanyl, thiophenyl, pyranyl, pyridinyl, isoquinolinyl, and pyrimidinyl.

As used herein, the term "alkoxy" and related terms, such as "alkoxy group(s)", means an alkyl group which includes at least one carbon atom, such as 1 to 20 carbon atoms, such as $C_1$-$C_{20}$ alkoxy, or $C_1$-$C_{10}$ alkoxy, or $C_1$-$C_6$ alkoxy. Examples of alkoxy groups include, but are not limited to, those examples of alkyl groups recited previously herein, which include a terminal divalent oxygen linkage or group (or terminal ether linkage or group), such as, but not limited to, methoxy ($CH_3$—O—), ethoxy ($CH_3CH_2$—O—), n-propoxy ($CH_3CH_2CH_2$—O—), iso-propoxy, linear or branched butoxy, linear or branched pentoxy, linear or branched hexoxy, etc.

As used herein, the term "halogen" and related terms, such as "halogen group(s)" and/or "halo group(s)", means a single bonded halogen atom, such as selected from fluoro (F), chloro (Cl), bromo (Br), and/or iodo (I).

As used herein, and unless otherwise explicitly stated, the term "hydrogen" and related terms, such as "hydrogen group(s)", means a single bonded hydrogen (—H).

As used herein, recitations of "substituted" group means a group including, but not limited to, aliphatic groups, cycloaliphatic groups, heterocycloaliphatic groups, aryl groups, or heteroaryl groups, in which at least one hydrogen thereof has been replaced or substituted with a group that is other than hydrogen, such as, but not limited to alkoxy groups; halo groups (e.g., F, Cl, I, and Br); hydroxyl groups; thiol groups; alkylthio groups; arylthio groups; ketone groups; aldehyde groups; carboxylic acid groups; carboxylic acid ester groups; phosphoric acid groups; phosphoric acid ester groups; sulfonic acid groups; sulfonic acid ester groups; nitro groups; cyano groups; alkyl groups (including aralkyl groups); alkenyl groups; alkynyl groups; haloalkyl groups; perhaloalkyl groups; heterocycloalkyl groups; aryl groups (including alkaryl groups, including hydroxyl substituted aryl, such as phenol); heteroaryl groups; amino groups, such as —N($R^{11'}$)($R^{12'}$) where $R^{11'}$ and $R^{12'}$ are each independently selected, for example, from hydrogen, aliphatic groups, cycloaliphatic groups, heterocycloaliphatic groups, aryl, and heteroaryl; carboxylate groups (—O—C(O)—R, where R is, for example, selected from aliphatic groups, cycloaliphatic groups, heterocycloaliphatic groups, aryl, and heteroaryl); siloxane groups; alkoxysilane groups; polysiloxane groups; amide groups; carbamate groups; carbonate groups; urea groups; polyester groups; polyether groups; polycarbonate groups; polyurethane groups; acrylate groups; methacrylate groups; nitrogen-containing heterocycles; or combinations thereof, including those classes and examples as described herein.

With reference to Formula (II), and with some embodiments, P is selected from hydrogen; alkyl; alkoxy (—O—R' where R' is selected from aliphatic group, cycloaliphatic group, heterocycloaliphatic group, aryl, and heteroaryl); acrylate ($CH_2$=CHC(O)O—); or methacrylate $CH_2$=C($CH_3$)C(O)O—).

With further reference to Formula (II), and in accordance with some further embodiments, P is selected from acrylate ($CH_2$=CHC(O)O—), methacrylate ($CH_2$=C($CH_3$)C(O)O—); trihalomethacrylate ($CH_2$=C($CX_3$)C(O)O— where each X independently is a halogen or halo group); cyanoacrylate ($CH_2$=C(CN)C(O)O—); oxirane

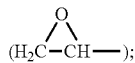

hydroxyl (—OH); primary amino (—$NH_2$); carboxylic acid (—C(O)OH); or carboxylic acid ester. Examples of trihalomethacrylate from which P can be selected include, but are not limited to, trifluoromethacylate and trichloromethacylate.

In accordance with some embodiments, and with reference to Formulas (II) and (III); subscript d in each case is independently 0 to 20, or 0 to 15, or 0 to 12, or 0 to 10, or 0 to 8, or 0 to 5; and subscripts e, f, and g, for each occurrence, are independently 0 to 3, such as 0, 1, 2, or 3.

With further reference to Formulas (II) and (III), $S_1$, $S_2$, $S_3$, and $S_4$, for each occurrence, are independently selected from a spacer unit chosen from: —$CH_2$—; —O—; —C(O)—; —N=N—; —CH=CH—; —C≡C—; —CH=N—; —$CF_2$—; or —NH—, provided that when two spacer units comprising heteroatoms are linked together the spacer units are linked so that heteroatoms are not directly linked to each other. Adjacent spacer units can together form various divalent linkages, such as, but not limited to alkyl linkages; ether linkages; carboxylic acid ester linkages, —O—C(O)— and/or —C(O)—O—; carbonate linkages, —O—C(O)—O—; amide linkages, —NH—C(O)— and/or —C(O)—NH—; urea linkages, —NH—C(O)—NH—; carbamate linkages, —O—C(O)—NH— and/or —NH—C(O)—O—; dione linkages, —C(O)—C(O)—; and combinations thereof, provided that the spacer units are linked so that heteroatoms are not directly linked to each other. For purposes of non-limiting illustration, and with some embodiments, spacer units being linked so that heteroatoms are not directly linked to each other, means, but is not limited to, —O— not being bonded directly to —O—; —NH— not being bonded directly to —NH—; —O— and —NH— not being bonded directly to each other; —N=N— not being bonded directly to —N=N—; —N=N— not being bonded directly to —O—; —N=N— not being bonded directly to —NH—; the nitrogen of —CH=N— not being bonded directly to the N of —CH=N—; or the N of —CH=N— not being bonded directly to —O—, —NH—, or —N=N—.

In accordance with some embodiments, and with reference to Formulas (II) and (III), $S_1$, $S_2$, $S_3$, and $S_4$, for each occurrence, are independently selected from a spacer unit chosen from: —$(CH_2)_e$—, —O—$_f$, —C(O)—$_g$ and —NH—; subscripts e, f, and g for each occurrence, are independently 0 to 3 (such as 0, 1, 2, or 3); provided that when two spacer units including heteroatoms are linked together the spacer units are linked so that heteroatoms are not directly linked to each other.

Independently for Formula (II) and Formula (III), and in accordance with some embodiments, $Q_1$, $Q_2$, and $Q_3$, for each occurrence, are independently a divalent group selected from the group consisting of unsubstituted or substituted cycloalkyl; unsubstituted or substituted phenyl; unsubstituted or substituted naphthyl; and unsubstituted or substituted triptycenyl; where the cycloalkyl substituents, phenyl substituents, naphthyl substituents, and triptycenyl substituents, and are each independently selected from cyano or —$(S_1)_d$—P, where $S_1$, d, and P are each as defined with regard to Formula (II).

Independently for Formula (II) and Formula (III), and in accordance with some further embodiments, $Q_1$, $Q_2$, and $Q_3$ for each occurrence, are independently a divalent group selected from the group consisting of unsubstituted or substituted 1,4-cyclohexyl; unsubstituted or substituted 1,4-phenyl; unsubstituted or substituted 1,5-naphthyl; unsubstituted or substituted 2,6-naphthyl; unsubstituted or substituted 1,8-naphthyl; and unsubstituted or substituted 1,4-triptycenyl, where the 1,4-cyclohexyl substituents, 1,4-phenyl substituents, 1,5-naphthyl substituents, 2,6-naphthyl substituents, 1,8-naphthyl substituents, and 1,4-triptycenyl substituents are each independently selected from cyano or —$(S_1)_d$—P, where $S_1$, d, and P are each as defined with regard to Formula (II).

With some embodiments of the present invention, for Formula (II), P is selected from hydrogen, alkyl, alkoxy, acrylate, or methacrylate; and Formula (IV) is further described as follows. For Formula (IV), (i) y is 1 to 30; (ii) each A independently for each y is a divalent group selected from the group consisting of alkyl and haloalkyl; (iii) each B independently for each y is a divalent group selected from the group consisting of: —O—; —C(O)O—; —OC(O)O—; —C(O)N($R_1$)— where $R_1$ is H or alkyl;

—NH—C(O)O—; —N(R$_2$)C(O)N(R$_2$)— where each R$_2$ is independently selected from H or alkyl;

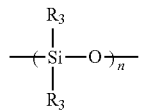

where n is 1 to 5, and each R$_3$ independently for each n is selected from methyl or phenyl; and —Si(R$_4$)(R$_4$)— where each R$_4$ is independently selected from methyl or phenyl; and (iv) E is a divalent group selected from the group consisting of alkyl groups and haloalkyl groups.

With some embodiments of the mesogen-containing compound of the present invention, Mesogen-1 is represented by Formula (II), where P of Formula (II) is selected from acrylate, methacrylate, trihalomethacrylate, cyanoacrylate, oxirane, hydroxyl, primary amino, carboxylic acid, or carboxylic acid ester; and Mesogen-3 is represented by the following Formula (V),

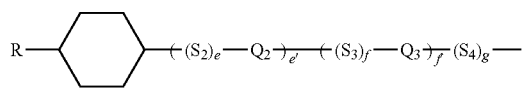

(V)

With reference to Formula (V), and in accordance with some embodiments, R is selected from hydrogen, halogen, alkyl, haloalkyl, alkoxy, or haloalkoxy; and S$_2$, S$_3$, S$_4$, Q$_2$, Q$_3$, e', f', e, and f are each independently as defined herein with regard to Formula (II). For purposes of non-limiting illustration, Formula (V) can be derived from Formula (II), when subscript d is 0; Q$_1$ is divalent 1,4-cyclohexyl; and P is R, where R is selected from certain P-groups, such as, hydrogen, halogen, alkyl, haloalkyl, alkoxy, or haloalkoxy.

With some further embodiments of the present invention, Mesogen-1 and Mesogen-3 are each independently represented by Formula (V), where: R is selected from hydrogen, halogen, alkyl, haloalkyl, alkoxy, or haloalkoxy; and S$_2$, S$_3$, S$_4$, Q$_2$, Q$_3$, e', f', e, and f are each independently as defined with regard to Formula (II).

With some additional embodiments of the present invention, Mesogen-1 and Mesogen-3 are each represented by Formula (V), and Mesogen-1 and Mesogen-3 are the same.

With reference to Formula (I), and in accordance with some embodiments, -L$^1$- and -L$^2$- each independently include at least 20 bonds, or at least 25 bonds, or at least 30 bonds, such as: 20 to 200 bonds (or 25 to 200 bonds, or 30 to 200 bonds); or 20 to 150 bonds (or 25 to 150 bonds, or 30 to 150 bonds); or 20 to 100 bonds (or 25 to 100 bonds, or 30 to 100 bonds); or 20 to 80 bonds (or 25 to 80 bonds, or 30 to 80 bonds); or 20 to 75 bonds (or 25 to 75 bonds, or 30 to 75 bonds); or 20 to 70 bonds (or 25 to 70 bonds, or 30 to 70 bonds); or 20 to 60 bonds (or 25 to 60 bonds, or 30 to 60 bonds); or 20 to 45 bonds (or 25 to 45 bonds, or 30 to 45 bonds), where each bond is independently selected from a single bond, a double bond, or a triple bond.

With some embodiments, the linking group -L$^1$-, that links Mesogen-1 and Mesogen-2 together; and the linking group -L$^2$-, that links Mesogen-2 and Mesogen-3 together, are in each case free of mesogen properties (linking group -L$^1$- is free of mesogen properties and is non-mesogenic; and linking group -L$^2$- is free of mesogen properties and is non-mesogenic).

In accordance with some embodiments, -L$^1$- and -L$^2$- of Formula (I) are each independently selected from the following Formulas L(1) through L(22), including combinations of two or more thereof:

L(1)
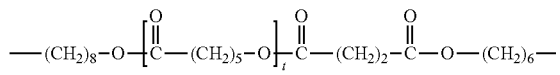

L(2)
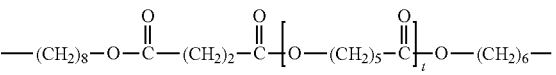

L(3)
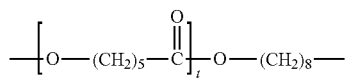

L(4)
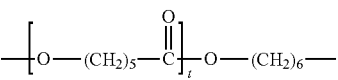

L(5)
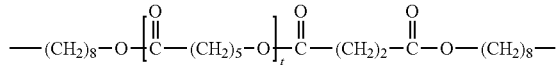

L(6)
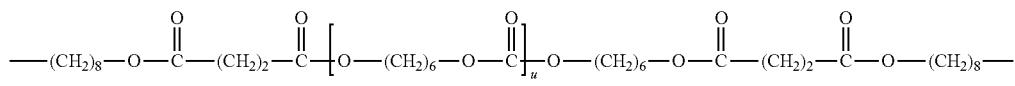

L(7)
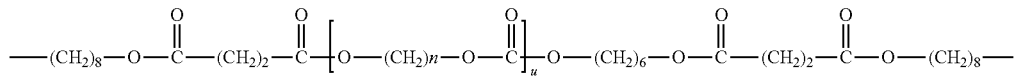

n = 5 or 6, 1:1

L(8)
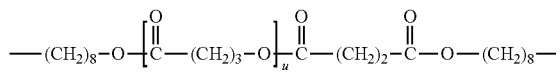

L(9)
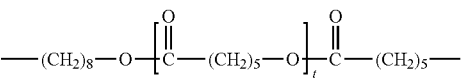

L(10)
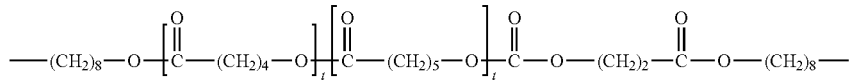

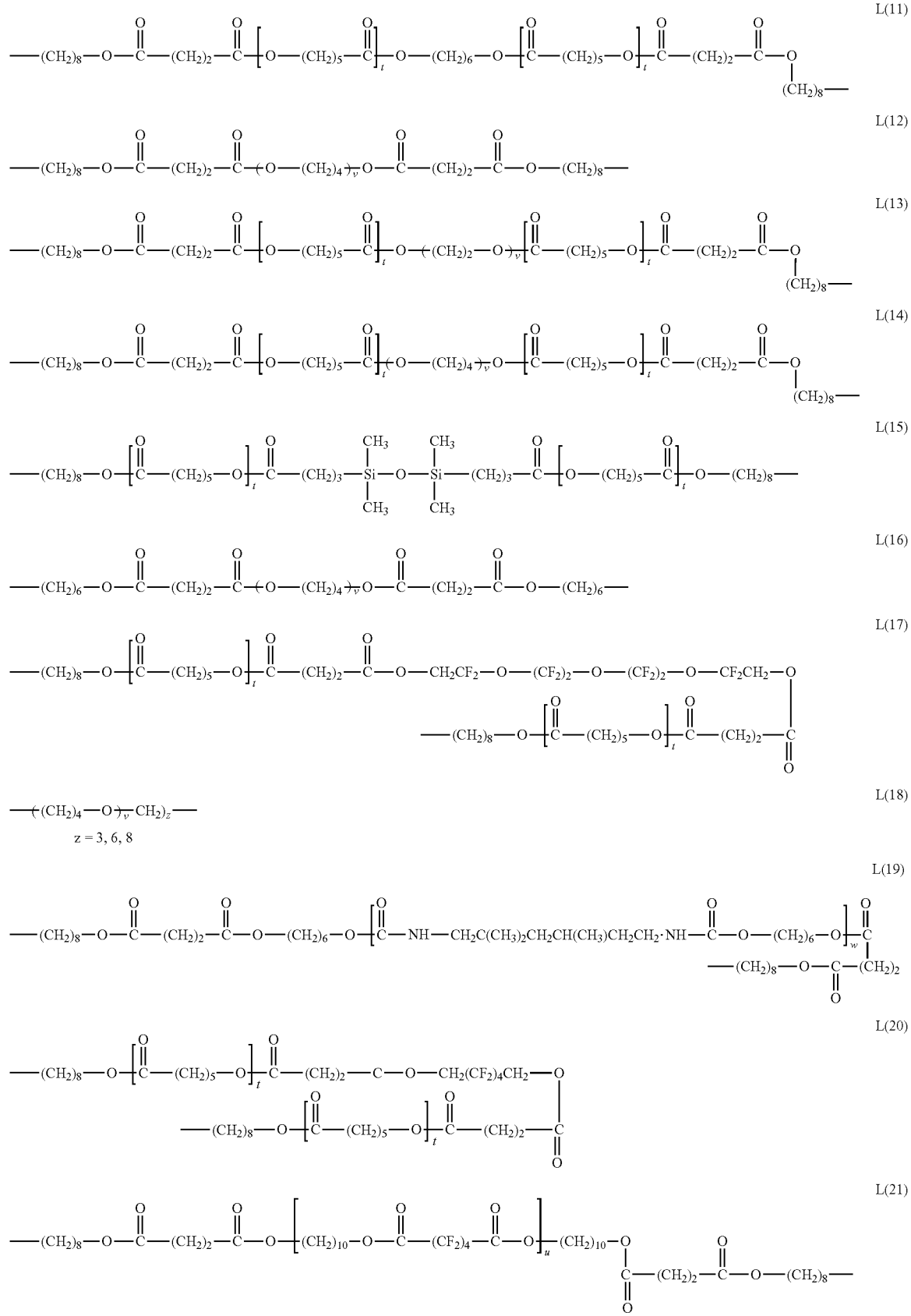

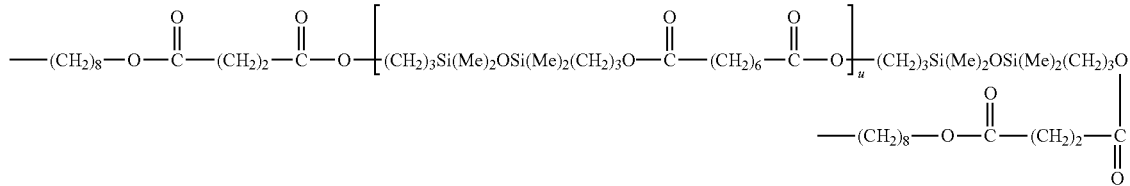

With reference to Formulas L(1) through L(22), each t, each u, each v, and each w, for each occurrence, are each independently from 1 to 20.

The present invention relates to a liquid crystal composition that includes the mesogen-containing compound(s) of the present invention, such as described with reference to Formula (I). Liquid crystal compositions according to the present invention, in some embodiments, in addition to at least one compound represented by Formula I, can further include at least one of a photochromic compound, a dichroic compound, and/or a photochromic-dichroic compound.

Classes of photochromic compounds that can be present in the liquid crystal compositions of the present invention include, but are not limited to, indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, non-thermally reversible photochromic compounds, and mixtures thereof.

Photochromic-dichroic compounds that can be present in the liquid crystal compositions of the present invention typically include at least one photochromic moiety; and at least one covalently bonded lengthening group, which can include at least one mesogenic segment. With some embodiments, each photochromic moiety of the photochromic-dichroic compound is selected from indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, non-thermally reversible photochromic compounds, and combinations thereof.

Classes and examples of lengthening groups of the photochromic-dichroic compounds that can be included in the liquid crystal compositions of the present invention include, but are not limited to, those described at columns 37-51 of U.S. Pat. No. 9,334,439 B2, which disclosure is incorporated herein by reference.

Liquid crystal compositions according to the present invention can optionally further include at least one additive. Examples of such optional additives include, but are not limited to, liquid crystal materials, liquid crystal property control additives, non-linear optical materials, dyes (e.g., static dyes), dichroic dyes, blue light blocking (or filtering) agents, alignment promoters, kinetic enhancers, photoinitiators, thermal initiators, surfactants, polymerization inhibitors, solvents, light stabilizers, thermal stabilizers, mold release agents, rheology control agents, gelators, leveling agents, free radical scavengers, coupling agents, tilt control additives, block or non-block polymeric materials, and/or adhesion promoters. Classes and examples of blue light blocking (or filtering) agents include, but are not limited to, those described in U.S. Pat. No. 9,683,102 B2 and US 2015/0234208 A1, the pertinent portions of which are incorporated herein by reference.

Examples of dichroic dyes that can be included in the liquid crystal compositions of the present invention include, but are not limited to, azomethines, indigoids, thioindigoids, merocyanines, indans, quinophthalonic dyes, perylenes, phthaloperines, triphenodioxazines, indoloquinoxalines, imidazo-triazines, tetrazines, azo and (poly)azo dyes, benzoquinones, naphthoquinones, anthroquinone and (poly)anthroquinones, anthropyrimidinones, iodine, iodates, or combinations of two or more thereof.

In accordance with the present invention, there is further provided an optical element that includes a substrate; and a layer on (or over) at least a portion of a surface of the substrate, in which the layer includes at least one mesogen-containing compound according to the present invention.

The substrate of the optical element, with some embodiments, is an optical substrate, which can include organic materials (such as organic polymers), inorganic materials, or combinations thereof (for example, composite materials). Examples of substrates that can be included in the optical elements of the present invention include, but are not limited to, those described at column 35, line 5 through column 36, line 57 of U.S. Pat. No. 8,628,685 B2, which disclosure is incorporated herein by reference.

The layer(s) provided over the substrate of the optical elements of the present invention include, with some embodiments, an organic matrix, such as an organic polymer matrix, which can be a cured (or crosslinked) organic matrix, or a thermoplastic organic matrix. Correspondingly, each layer of the optical elements of the present invention can be selected from cured (or crosslinked) layers and thermoplastic layers. The organic matrix of each layer of the optical elements of the present invention can include linkages such as, but not limited to, ether linkages; carboxylic acid ester linkages; urethane linkages; amide linkages; urea linkages; carbonate linkages; linkages formed from the radical polymerization of radically polymerizable ethylenically unsaturated groups, such as, but not limited to, vinyl groups, allyl groups, and/or (meth)acrylate groups; and combinations of two or more thereof.

Each layer of the optical elements of the present invention can be formed by art-recognized methods, such as, but not limited to, lamination methods and coating methods. Coating methods include, but are not limited to, spray coating methods; spin coating methods; curtain coating methods; dip coating methods; micro jet coating methods (such as ink jet coating methods); in-mold coating methods; and combinations thereof. Lamination methods include, but are not limited to, extrusion lamination methods (such as directly over the substrate); in-mold lamination methods (in which a laminate is placed in a mold, and the substrate is formed there-against within the mold); thermal lamination methods (in which a laminate is thermally fused over the substrate); adhesive lamination methods (in which the laminate is adhered over the substrate by an interposed adhesive layer); and combinations thereof.

With some embodiments of the present invention, the optical element further includes an alignment layer interposed between the substrate and the layer (which includes a mesogen-containing compound of the present invention), in which the alignment layer is at least partially alignable by exposure to at least one of a magnetic field, an electric field, linearly polarized radiation, shear force, or combinations of two or more thereof. Classes and examples of materials that can be used as or to form the alignment layer include, but are not limited to, the orientation facilities, orientation materials, alignment media, and alignment facilities described at column 5, line 5 through column 6, line 4; column 7, line 56 through column 24, line 36; and the examples of U.S. Pat. No. 8,926,091 B2, which disclosure is incorporated herein by reference.

The optical element of the present invention can, with some embodiments, include one or more additional layers, such as, but not limited to, primer layer(s), antireflective layer(s), protective layer(s), hardcoat layer(s), or polarizing layer(s). Classes and examples of such additional optional layers are described at column 20, line 30 through column 21, line 38 of U.S. Pat. No. 8,828,284 B2, which disclosure is incorporated herein by reference.

With some embodiments, the optical element of the present invention is selected from an ophthalmic element, a display element, a window, a mirror, or a liquid crystal cell element.

With some further embodiments, the ophthalmic element of the present invention is selected from a corrective lens, a non-corrective lens, a contact lens, an intra-ocular lens, a magnifying lens, a protective lens, or a visor.

The present invention is more particularly described in the following examples, which are intended as illustrative only, since numerous modifications and variations therein will be apparent to those skilled in the art.

EXAMPLES

In Part 1 of the following examples, there is described the preparation of terminal and internal (or central) mesogen-containing portions or segments. In Part 2 there is described the preparation of trimesogen compounds according to the present invention (Examples 1-8), which include non-mesogenic linking groups that connect (covalently bond) together terminal and internal mesogen-containing portions thereof, and comparative mesogen-containing compounds (CE-9 and CE-10). In Part 3 there is described the preparation of liquid crystal coating formulations. In Part 4 there is described the preparation of coated substrates (test specimens). In Part 5 there is described the photochromic performance testing of the test specimens.

Part 1

Synthesis of Mesogen-Containing Segments

Part 1a. Synthesis of Terminal Mesogen-Containing Segments S1 Through S6.

The synthesis of terminal mesogen-containing segments S1 through S6 is described as follows. Representative structures for mesogen-containing segments S1 through S6 are provided Table 1 below.

Segment S1

Segment S1 was prepared in accordance with Example 1, step 8 of United States Patent Application Publication No. US 2017/0275534 A1, which particular disclosure is incorporated herein by reference.

Segment S2

To a one-neck, round bottom flask containing Segment S1 (400 g) and succinic anhydride (74.0 g) was added toluene (1.5 L) and triethylamine ("Et$_3$N," 15.0 mL). The suspension was heated to 80° C. and stirred for 5 hours. The reaction mixture was poured into hot ethyl acetate ("EtOAc," 1.5 L, 65° C.) over 5 minutes while stirring, then the flask was rinsed with tetrahydrofuran ("THF," 100 mL). The resulting solution was allowed to cool to room temperature and crystallized overnight to yield 410 g of product (yield 88%).

Segment S3

Segment S3 was prepared in accordance with Example 1, Step 5 of United States Patent Application Publication No. US 2012/0002141 A1, which particular disclosure is incorporated herein by reference.

Segment-S4

4-((4-((6-(Acryloyloxy)hexyl)oxy)benzoyl)oxy)phenyl 4-((8-hydroxyoctyl)oxy)benzoate was prepared using the procedures of Steps 1 to 6 of Example 2 in U.S. Pat. No. 8,349,210 B2 substituting 6-chlorohexan-1-ol in place of 3-chloropropan-1-ol in Step 1, and 8-chlorohexan-1-ol in place of 6-chlorohexan-1-ol in Step 3, which particular disclosure is incorporated herein by reference.

Segment S5

Segment S5 was prepared in accordance with Example 8, Step 2 in United States Patent Application Publication No. US 2012/0002141 A1, which particular disclosure is incorporated herein by reference.

Segment S6

4-((8-(4-((4-((4-Methylbenzoyl)oxy)phenoxy)carbonyl) phenoxy)octyl)oxy)-4-oxobutanoic acid was prepared using the procedures of Segment S2, replacing Segment S1 with an equimolar amount of the product of Step 2 of Example 8 from U.S. Pat. No. 8,349,210 B2, which particular disclosure is incorporated herein by reference.

TABLE 1

Representative Structures of
Terminal Mesogen-Containing Segments S1 through S6

| Segment No. | Representative Structures |
|---|---|
| S1 | 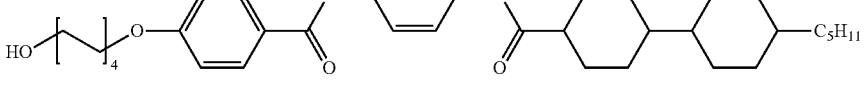 |
| S2 | 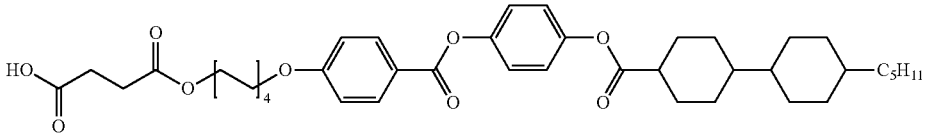 |
| S3 | 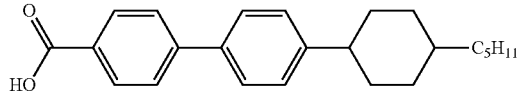 |
| S4 | 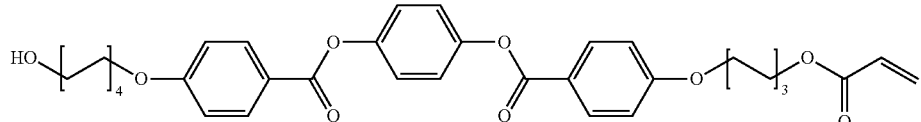 |
| S5 | 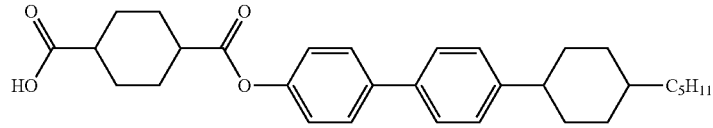 |
| S6 | 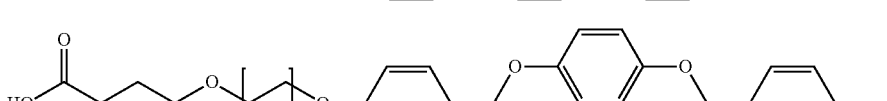 |

Part 1b. Synthesis of Central Mesogen-Containing Segments S7 Through S11.

The synthesis of central mesogen-containing segments S7 through S11 is described as follows. Representative structures for mesogen-containing segments S7 through S11 are provided Table 2 below.

Segment S7

Step 1

Methylhydroquinone (12.41 g), 4-((6-((tetrahydro-2H-pyran-2-yl)oxy)hexyl)oxy)benzoic acid (70.9 g), dimethylaminopyridine ("DMAP," 4.88 g), and dichloromethane ("DCM", 500 mL) were added to N,N'-dicyclohexylcarbodiimide ("DCC," 51.5 g). After stirring for 3 hours at room temperature, the formed dicyclohexylurea was removed and the filtrate passed through a silica plug (eluent was DCM).

Step 2

The product from Step 1 was dissolved in methanol-DCM ("MeOH-DCM" 200 mL/200 mL), to which was then added 4-toluenesulfonic acid ("TsOH," 3.8 g). After stirring at room temperature for 2 hours, the solvent was removed and the residue dissolved in DCM. The solution was washed twice with aqueous NaHCO$_3$ then purified by column chromatography.

Segment S8

Step 1

The procedures of Segment S7, Step 1 were carried out using the following reagents: 4-hydroxy-2/3-methylphenyl 4-((6-((tetrahydro-2H-pyran-2-yl)oxy)hexyl)oxy)benzoate (10.7 g), 4-((4-((6-((tetrahydro-2H-pyran-2-yl)oxy)hexyl) oxy)benzoyl)oxy)benzoic acid (11.05 g), DMAP (0.61 g), DCC (6.7 g), and DCM 300 mL. The resulting solid was purified by dissolving in EtOAc, filtering, then precipitating from EtOAc-MeOH.

Step 2

Synthesis of 4-((4-((4-((6-hydroxyhexyl)oxy)benzoyl) oxy)-2/3-methylphenoxy)carbonyl)phenyl 4-((6-hydroxyhexyl)oxy)benzoate was accomplished following the procedures of Segment S7, Step 2 using the following reagents: product of Step 1 above (21.3 g), MeOH-DCM (150 mL/150 mL), TsOH (0.95 g). The product was recrystallized from DCM-EtOAc then dissolved in hot CHCl$_3$ before being passed through a silica gel plug. Yield: 9.0 g.

Segment S9

Step 1

Triptycene-1,4-hydroquinone (prepared in accordance with compound 2 from *J. Mat. Chem. A*, 2014, 2, 13309-

13320, 15.0 g), 4-((8-((tetrahydro-2H-pyran-2-yl)oxy)octyl) oxy)benzoic acid (40.4 g), DCM (250 ml), and DMAP (1.28 g), were added to DCC (26.97 g). After stirring for 3 hours at room temperature, the formed dicyclohexylurea was removed and the filtrate passed through a silica plug (eluent was DCM).

Step 2

The product from Step 1 was dissolved in THF-EtOH (200 ml/100 ml), to which was then added TsOH (2.2 g). After stirring at room temperature for 2 hours, the solvent was removed and the residue dissolved in DCM. The solution was washed twice with aqueous NaHCO$_3$ then purified by column chromatography.

Segment S10

Step 1

To a reaction flask containing 6-bromohexyl methacrylate (25.00 g), 2,5-dihydroxybenzoic acid (15.46 g), Et$_3$N (10.66 g) and a catalytic amount of 3,5-di-tert-butyl-4-hydroxytoluene ("BHT", 0.5 g) was added N,N-dimethylformamide ("DMF", 100 mL). After stirring and heating at 90° C. for 4 hours the resulting solution was poured into cold water (200 mL). Once extracted with EtOAc (3×150 mL), the combined organic layers were washed with brine (3×200 mL), dried over MgSO$_4$, and filtered through a short pad of silica-gel. A concentration step yielded a light brown liquid (33 g).

Step 2

Synthesis of 2-(((6-(methacryloyloxy)hexyl)oxy)carbonyl)-1,4-phenylene bis(4-((8-((tetrahydro-2H-pyran-2-yl) oxy)octyl)oxy)benzoate) was accomplished following the procedures of Segment S7, Step 1 using the following reagents: product of Step 1 above (5.0 g), 4-((8-((tetrahydro-2H-pyran-2-yl)oxy)octyl)oxy)benzoic acid (11.95 g), DMAP (0.378 g), DCC (8.00 g), BHT (0.2 g), and DCM (250 mL).

Step 3

Synthesis of 2-(((6-(methacryloyloxy)hexyl)oxy)carbonyl)-1,4-phenylene bis(4-((8-hydroxyoctyl)oxy)benzoate) was accomplished following the procedures of Segment S7, Step 2 using the following reagents: product from Step 2 above (15.0 g), TsOH (1.0 g), THF (200 mL), EtOH (100 mL), and BHT (0.25 g).

Segment S11

Step 1

Decafluorobiphenyl (5.00 g), 1,6-hexanediol (14.21 g), and K$_2$CO$_3$ (8.58 g) were stirred under nitrogen in DMF (75 mL) at room temperature for 36 hours. Water was added and the solution cooled on ice for 30 minutes before the resulting precipitate was filtered. The material was concentrated onto silica and chromatographed (eluent was 25% EtOAc in hexanes) to give a white solid. Yield: 5.98 g, 75%.

Step 2

The product of Step 1 (6.00 g) was reacted with succinic anhydride (2.49 g) and Et$_3$N (0.47 mL) under the same conditions as those described for Segment S2 to form 4,4'-(((((perfluoro-[1,1'-biphenyl]-4,4'-diyl)bis(oxy))bis (hexane-6,1-diyl))bis(oxy))bis(4-oxobutanoic acid).

TABLE 2

Representative Structures of Central Mesogen-Containing Segments S7 through S11.

| Segment No. | Representative Structures |
|---|---|
| S7 | |
| S8 | |
| S9 | |
| S10 | |

TABLE 2-continued

Representative Structures of
Central Mesogen-Containing Segments S7 through S11.

| Segment No. | Representative Structures |
|---|---|
| S11 | 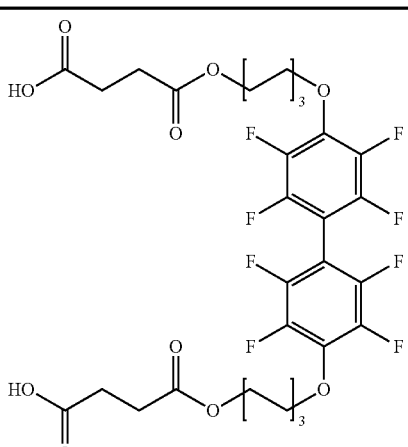 |

Part 2

Preparation of Trimesogen Compounds

The following provides a description of the preparation of trimesogen compounds according to the present invention (Examples 1-8), which include non-mesogenic linking groups that connect (covalently bond) together terminal and internal mesogen-containing portions thereof, and comparative mesogen-containing compounds (CE-9 and CE-10). Representative structures of Examples 1-8, and Comparative Examples CE-9 and CE-10 are provided in Table 4.

Example 1

Segment S1 (8.00 g) and ε-caprolactone (5.88 g) were dissolved in DCM, followed by addition of diphenyl phosphate ("DPP") (0.82 g). After stirring at room temperature for 4 hours, Segment S11 (4.71 g) and DMAP (0.79 g) were added, and once dissolved in DCC (3.42 g) was added in one portion. The material was dissolved in EtOAc, filtered through celite, then precipitated from MeOH/EtOAc to give the desired product. Yield: 16.29 g, 89%.

Example 2

Step 1

Segment S4 (10.00 g) and ε-caprolactone (7.2 g) were dissolved in DCM, followed by the addition of DPP (1.98 g). After stirring at room temperature for 4 hours, 4-((4-((6-((tetrahydro-2H-pyran-2-yl)oxy)hexyl)oxy)benzoyl)oxy) benzoic acid (7.69 g) and DMAP (0.96 g) were added, and once dissolved DCC (4.5 g) was added in one portion. The material was dissolved in EtOAc, filtered through celite and concentrated. Yield: 22 g.

Step 2

The product of step 1 above (22 g) was dissolved in MeOH-DCM (50 mL/50 mL). To this was added TsOH (0.6 g). After stirring at room temperature for 2 hours, the solvent was removed and the residue dissolved in DCM. The solution was washed twice with aqueous $NaHCO_3$ then purified by column chromatography.

Step 3

The product of step 2 above and ε-caprolactone (7.3 g) were dissolved in 150 mL DCM, followed by addition of DPP (2.0 g). After stirring at room temperature for 4 hours, Segment S2 (12.1 g) and DMAP (0.98 g) were added, and once dissolved DCC (4.0 g) was added in one portion. The material was dissolved in EtOAc, filtered through celite, then precipitated from MeOH/EtOAc to give the desired product. Yield: 20 g.

Examples 3-8

For the trimesogen compounds of Examples 3 through 8, the following general procedure was followed, using the materials listed in TABLE 3. The designated central mesogen-containing segment (1 equivalent) was dissolved in dichloromethane along with ε-caprolactone in the molar ratios recited in TABLE 3. To this was added DPP (0.5 equivalents) and the mixture was stirred under nitrogen for 4 hours to form a new diol. The resulting diol was subsequently reacted with the designated terminal mesogen-containing segments (2.05-2.6 equivalents) by adding DCC (2.17-2.8 equivalents) and DMAP (0.3-1.0 equivalents). After stirring at room temperature overnight under nitrogen, the dicyclohexylurea precipitate was removed and the filtrate partially concentrated before being passed through a plug of silica. The material was dissolved in EtOAc and filtered through celite, then precipitated from MeOH/EtOAc to give the desired product.

TABLE 3

Components used to Synthesize the Trimesogen Compounds of Examples 3-8.

| Example No. | Central segment (1 eq) | ε-caprolactone equivalents | Terminal segment (2 eq) | Yield |
|---|---|---|---|---|
| 3 | S7 | 8.0 | S2 | 73% |
| 4 | S8 | 8.5 | S2 | 80% |
| 5 | S9 | 6.0 | S2 | 30% |
| 6 | S10 | 6.0 | S2 | 51% |
| 7 | S8 | 8.5 | S3 | 70% |
| 8 | S7 | 8.0 | S5 | 89% |

COMPARATIVE EXAMPLES

CE-9

A comparative trimesogen was prepared according to the methods of Examples 3-8, using 1 equivalent Segment S7 as the central segment, 8.0 equivalents of ε-caprolactone, and 2 equivalents Segment S6 as the terminal segment to obtain the desired product in 85% yield.

CE-10

Step 1

4'-Hydroxy-[1,1'-biphenyl]-4-carboxylic acid (7.52 g), 5-chloropentan-1-ol (16.51 g), KI (2.91 g), and $K_2CO_3$ (19.53 g) were stirred in DMF at 60° C. while under nitrogen. After stirring overnight, water was added causing the product to precipitate. After cooling on ice for 45 minutes, the precipitate was filtered and washed with water. The crude product was recrystallized from EtOH to give a white solid. Yield: 6.00 g, 44%.

Step 2

The product from Step 1 above (6.00 g), 4'-hydroxy-[1,1'-biphenyl]-4-carbonitrile (6.21 g), and $PPh_3$ (11.20 g) were dissolved in DCM before diisopropyl azodicarboxylate (8.67 g) was added over 2 minutes. After stirring for an hour, the crude reaction mixture was recrystallized from EtOAc/EtOH (450 mL/50 mL) to give a white solid. Yield: 2.62 g, 23%.

TABLE 4

Representative Structures for Examples 1-8, and Comparative Examples CE-9 and CE-10

| Example | Representative Structure[a] |
|---|---|
| 1 | |
| 2 | |
| 3 | |

TABLE 4-continued

Representative Structures for Examples 1-8, and Comparative Examples CE-9 and CE-10

| Example | Representative Structure[a] |
|---|---|
| 4 | |
| 5 | |
| 6 | |

TABLE 4-continued
Representative Structures for Examples 1-8, and Comparative Examples CE-9 and CE-10
| Example | Representative Structure[a] |
|---|---|
| 7 | 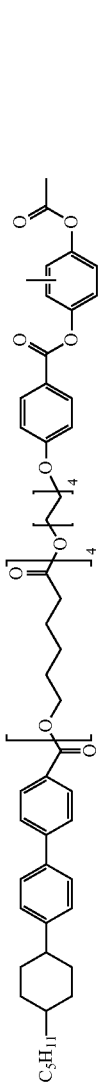 |
| 8 | 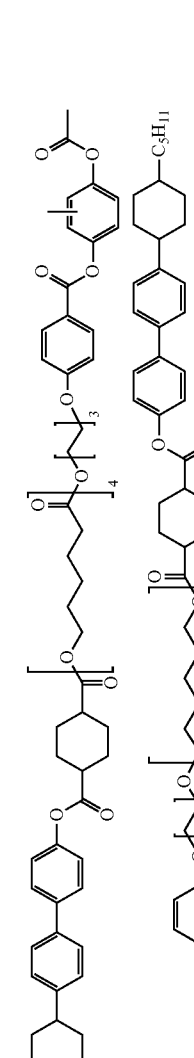 |
| CE-9 |  |
| CE-10 | 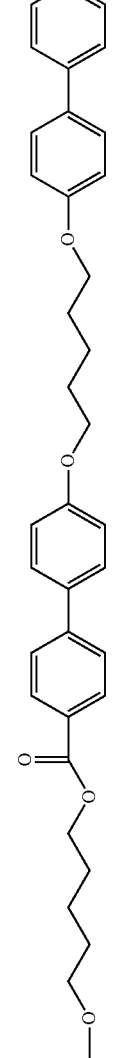 |
[a]1H NMR was used to confirm all product structures as well as the average oligomer lengths.

Part 3

Liquid Crystal Coating Formulations

Part 3a. Preparation of Standard Liquid Crystal Coating (LCC) Formulation

In suitable containers equipped with a stir bar, the first three ingredients, listed in the following Table 5, were charged and stirred at room temperature until a homogeneous solution was obtained. Then the mixture of photochromic dichroic dyes was charged and the resulting mixture was stirred for 1 hour at 90° C. The liquid crystal monomers were then charged and the solution stirred for an additional hour at 90° C. The temperature of the solution was then reduced to 60° C. and IRGACURE 819 photoinitiator was added to the solution and the mixture was stirred for 30 minutes to obtain the final solution.

TABLE 5

Standard Liquid Crystal Coating (LCC) Formulation

| Component | Amount (parts by weight) |
| --- | --- |
| Anisole | 1.995 |
| BYK ®-322[1] | 0.002 |
| 4-Methoxyphenol | 0.003 |
| Photochromic dichroic dyes[2] | 0.36 |
| RM257[3] | 1.26 |
| LCM-2[4] | 0.66 |
| LCM-3[5] | 0.54 |
| LCM-4[6] | 0.54 |
| IRGACURE ® 819[7] | 0.045 |

[1]An aralkyl modified poly-methyl-alkyl-siloxane available from BYK Chemie, USA.
[2]A mixture of photochromic-dichroic indenofused naphthopyran dyes formulated to give a grey color on activation.
[3]A liquid crystal monomer, available commercially from EMD Chemicals, Inc.
[4]4-((4-((8-((6-((6-((6-((6-((6-((6-(methacryloyloxy)hexanoyl)oxy)hexanoyl)oxy)hexanoyl)oxy) hexanoyl)oxy) hexanoyl)oxy) hexanoyl)oxy) octyl)oxy)benzoyl)oxy)phenyl 4'-pentyl-[1,1'-bi(cyclohexane)]-4-carboxylate, prepared according to procedures described in U.S. Pat. No. 7,910,019B2.
[5]1-(6-(6-(6-(6-(6-(6-(6-(8-(4-(4-(4-(6-acryloyloxyhexyloxy)benzoyloxy)phenoxycarbonyl)phenoxy)octyloxy)-6-oxohexyloxy)-6-oxohexyloxy)-6-oxohexyloxy)-6-oxohexyloxy)-6-oxohexyloxy)-6-oxohexyloxy)-6-oxohexanol, prepared in accordance with Example 17 in U.S. Pat. No. 7,910,019B2.
[6]3-methyl-4-((4-pentylcyclohexane-1-carbonyl)oxy)phenyl 4-((6-(acryloyloxy)hexyl)oxy)benzoate.
[7]A photoinitiator available from BASF.

Part 3b. Preparation of Liquid Crystal Coating Formulations Including Mesogen-Containing Compounds:

Liquid Crystal Coating Formulations including mesogen-containing compounds were prepared by adding certain mesogen-containing compounds to the Standard Liquid Crystal Coating Formulation described in Part 3a. The mixtures were prepared as summarized in the following Table 6, where each mesogen-containing compound was added to 100 parts Standard Liquid Crystal Coating Formulation. The components were combined and stirred at 80° C. for 1 hour to achieve a homogeneous solution. The additive quantities are calculated based on 4.4 mol % of monomers.

TABLE 6

| Example | Mesogen-Containing Compound | Parts by weight of Mesogen-Containing Compound |
| --- | --- | --- |
| Example 11 | Example 1 | 0.480 |
| Example 12 | Example 2 | 0.443 |
| Example 13 | Example 3 | 0.493 |
| Example 14 | Example 5 | 0.511 |
| Example 15 | Example 6 | 0.503 |
| Example 16 | Example 7 | 0.389 |
| Example 17 | Example 8 | 0.410 |
| CE-18 | Example CE-9 | 0.444 |
| CE-19 | Example CE-10 | 0.127 |
| CE-20 | None | None |

Part 4

Preparation of Coated Substrates

The following procedure was used to form coated substrates (test specimens). Each liquid crystal coating formulation described in Part 3 (Table 6) was spin coated at a rate of 400 revolutions per minute (rpm) for 6 seconds, followed by 1250 rpm for 6 seconds onto lens substrates prepared from CR-39® monomer having an alignment layer. Each coated substrate was placed in an oven at 60-75° C. for 30 minutes to facilitate alignment, after which they were cured under two ultraviolet lamps in a UV curing oven, designed and built by Belcan Engineering, under nitrogen while running on a conveyor belt at 2 ft/min (0.61 meters/min) speed at peak intensity of 0.388 Watts/cm$^2$ of UVA and 0.165 Watts/cm$^2$ of UVV; and UV dosage of 7.386 Joules/cm$^2$ of UVA and 3.337 Joules/cm$^2$ of UVV.

Part 5

Photochromic Performance Testing Including Absorption Ratio and Optical Response Measurements Prior to response testing on an optical bench, the test specimens were conditioned in a multistep custom built conditioning unit. First they were exposed to 365 nm ultraviolet light for 10 minutes at a distance of about 10 cm from the source of electromagnetic radiation, in order to pre-activate the photochromic compounds. The UVA irradiance at the sample was measured to be 7.7 Watts per square meter. Next, the test specimens were heated to 70° F. (21.1° C.) for 10 minutes. Finally, the heating element was turned off and F17T8 yellow halogen lights were turned on for 30 minutes in order to bleach, or inactivate, the photochromic compounds in the test specimens. The illuminance from these yellow halogen lights at the test specimens was measured to be 9.0 Klux. The test specimens were then kept in a dark environment for at least 1 hour prior to testing in order to cool and continue to fade back to a ground state.

An optical bench was used to measure the optical properties of the test specimens and derive the absorption ratio and photochromic properties. Each test specimen was placed on the optical bench with an activating light source positioned at a 30° to 35° angle of incidence to the surface of the test specimen. The activating light source used was a Xenon Arc Lamp powered by a Newport/Oriel Model 69911 300-Watt power supply fitted with a UNIBLITZ® VS-25 high-speed computer controlled shutter that momentarily closed during data collection so that stray light would not interfere with the data collection process, a SCHOTT® 3 mm KG-2 heat absorbing filter, which removed short wavelength radiation, neutral density filter(s) for intensity attenuation and a condensing lens for beam collimation. The arc lamp was equipped with a Digital Exposure Controller and sensor (Newport/Oriel model 68945) in order to maintain fine control of the output over time.

A broadband light source for monitoring response measurements was positioned in a perpendicular manner to the surface of the test specimen. Increased signal of shorter visible wavelengths was obtained by collecting and combining separately filtered light from a 100-Watt tungsten halogen lamp (controlled by a LAMBDA® ZUP60-14 constant voltage power supply) with a split-end, bifurcated fiber optical cable. Light from one side of the tungsten halogen lamp was filtered with a SCHOTT® KG1 filter to absorb heat and a HOYA® B-440 filter to allow passage of the shorter wavelengths. The other side of the light was either filtered with a SCHOTT® KG1 filter or unfiltered. The light was collected by focusing light from each side of the lamp onto a separate end of the split-end, bifurcated fiber optic cable, and subsequently combined into one light source emerging from the single end of the cable. A 4 to 6 inch (10.2 to 15.25 cm) light pipe was attached to the single end of the cable to ensure proper mixing. The broad band light source was fitted with a UNIBLITZ® VS-25 high-speed computer controlled shutter that momentarily opened during data collection.

Polarization of the light source was achieved by passing the light from the single end of the cable through a Moxtek, PROFLUX® Polarizer held in a computer driven (analyzer polarizer), motorized rotation stage (Model M-061.PD, M660, U651 or equivalent from Physik Instrumente). The monitoring beam was set so that the one polarization plane (0°) was perpendicular to the plane of the optical bench table and the second polarization plane (90°) was parallel to the plane of the optical bench table. The samples were run in air, at 23° C.±0.1° C. (which temperature was maintained by a temperature controlled air cell).

To align the test specimens prepared in Part 4, a second polarizer was added to the optical path (research grade film polarizer, such as a polarizer from OptoSigma, SPF-50C-32). The second polarizer was set to 90° (+/−0.1 degrees) of the first analyzer polarizer. The sample was placed in an air cell in a self-centering holder mounted on a rotation stage (Model M-061.PD, M660, U651 or equivalent from Physik Instrumente). A laser beam (Coherent-ULN 635 diode laser) was directed through the crossed polarizers and test specimen. The signal intensity of the laser beam was measured, in relative counts by the spectrophotometer. The sample was rotated 120 degrees in 3 degree increments in order to locate a minimum transmitted light intensity of the laser beam. The test specimen was then positioned near the minimum transmitted light intensity and then the test specimen was rotated 12 degrees in 0.1 degree steps in order to locate the minimum transmission to +/−0.1 degrees, depending upon the sample quality. The test specimen was then finally positioned at the minimum transmission angle. At this point the test specimen was aligned either parallel or perpendicular to the Moxtek analyzer polarizer. The second polarizer and the diode laser beam were removed from the optical path. Using this process, samples were aligned to ±0.1 degrees prior to any activation.

To conduct the measurements, each test specimen was exposed to roughly 6.7 W/m² of UVA from the activating light source for 15 minutes to activate the photochromic compounds. An International Light Research Radiometer (Model ILT950 (FC) with a detector system was used to verify exposure at the beginning of each day. Light from the monitoring source that was polarized to the 0° polarization plane was then passed through the sample and focused into a 1 inch (2.54 cm) integrating sphere, which was connected to an OCEAN OPTICS® S2000 spectrophotometer using a single function fiber optic cable. The spectral information, after passing through the sample, was collected using OCEAN OPTICS Drivers with propriety software from Transitions Optical, Ltd. While the photochromic material was activated, the position of the polarizer was rotated back and forth to polarize the light from the monitoring light source to the 90° polarization plane and back. Data was collected for approximately 600 to 1200 seconds at 5-second intervals during activation. For each test, rotation of the polarizers was adjusted to collect data in the following sequence of polarization planes: 0°, 90°, 90°, 0°, etc.

Absorption ratio (AR) is the ratio of absorbance measured at 90° polarization (perpendicular orientation with the analyzer polarizer, minimum transmission) and 0° polarization (parallel orientation with the analyzer polarizer, maximum transmission).

Change in optical density (ΔOD) from the bleached state (unactivated state) to the darkened state (activated state) was determined by establishing the initial transmittance, opening the shutter from the xenon lamp to provide ultraviolet radiation to change the test lens from the bleached state to an activated state. Data was collected at selected intervals of time, measuring the transmittance in the activated state, and calculating the change in optical density according to the formula: ΔOD=log(% Tb/% Ta), where % Tb is the percent transmittance in the bleached state, % Ta is the percent transmittance in the activated state and the logarithm is to the base 10.

The fade half-life (T½) is the time interval in seconds for the ΔOD of the activated form of the photochromic compounds in the test specimens to reach one half the ΔOD measured after fifteen minutes, or after saturation or near-saturation was achieved, at room temperature after removal of the source of activating light (e.g., by closing the shutter).

The photochromic performance test results (absorbance ratio and fade half-life) obtained from the Examples according to the present invention and Comparative Examples (CE) are summarized in the following Table 7.

TABLE 7

Photochromic Performance Test Results

| Example | AR | Fade (T½) |
|---|---|---|
| Example 11 | 7.0 | 189 |
| Example 12 | 5.5 | 177 |
| Example 13 | 6.7 | 184 |
| Example 14 | 5.9 | 200 |
| Example 15 | 5.8 | 203 |
| Example 16 | 5.5 | 166 |
| Example 17 | 5.4 | 158 |
| CE-18 | 4.6 | 186 |
| CE-19 | 4.6 | 218 |
| CE-20 | 4.5 | 227 |

The results summarized in Table 7 demonstrate that a coating layer including a mesogen-containing compound according to the present invention provides improved dichroic properties in the activated state (as indicated by AR values of greater magnitude), as compared to: the comparative examples which do not include any mesogen segment having at least four cyclic groups (CE-18 and CE-19); and the comparative example that does not include a mesogen-containing compound (CE-20). Improved dichroic properties were observed with mesogen-containing compounds according to the present invention having at least one mesogen with at least four cyclic groups in the terminal mesogen group(s), or the central mesogen group, or both. In addition, the mesogen-containing compounds according to the present invention provided equivalent or improved fade half-life values as compared to the comparative examples.

The present invention can be further characterized by one or more of the following non-limiting clauses 1-17.

Clause 1: A mesogen-containing compound represented by the following Formula (I), and as graphically illustrated by Formula (Ia) of FIG. 1 of the drawing, $$\text{(Mesogen-1)-L}^1\text{-(Mesogen-2)-L}^2\text{-(Mesogen-3)} \quad \text{(I)}$$

wherein (A) Mesogen-1 and Mesogen-3 are each independently represented by the following Formula (II),

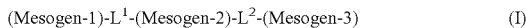

(II)

wherein for Formula (II),

P is selected from hydrogen, halogen, alkyl, haloalkyl, alkoxy, haloalkoxy, acrylate, methacrylate, trihalomethacrylate, cyanoacrylate, acrylamido, methacrylamido, oxirane, hydroxyl, primary amino, carboxylic acid, or carboxylic acid ester;

(B) Mesogen-2 is represented by the following Formula (III),

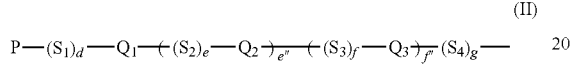

(III)

wherein independently for each of Formula (II) and Formula (III), $S_1$, $S_2$, $S_3$, and $S_4$, for each occurrence, are independently selected from a spacer unit chosen from —$CH_2$—; —O—; —C(O)—; —N=N—; —CH=CH—; —C≡C—; —CH=N—; —$CF_2$—; or —NH—, provided that when two spacer units comprising heteroatoms are linked together the spacer units are linked so that heteroatoms are not directly linked to each other;

d is 0 to 20;

e, f, and g, for each occurrence, are independently 0 to 3;

$Q_1$, $Q_2$, and $Q_3$, for each occurrence, are independently a divalent group selected from the group consisting of unsubstituted or substituted cycloaliphatic group; unsubstituted or substituted heterocycloaliphatic group; unsubstituted or substituted aryl; and unsubstituted or substituted heteroaryl; wherein the cycloaliphatic group substituents, heterocycloaliphatic group substituents, aryl substituents, and heteroaryl substituents are each independently selected from cyano or —$(S_1)_d$—P, where $S_1$, d, and P are each as defined with regard to Formula (II); and e" and f", for each occurrence, are independently from 0 to 6, provided the sum of e" and f" is at least 1 (or provided the sum of e" and f" is at least 2); and (C) -$L^1$- and -$L^2$- are each independently represented by the following Formula (IV), -(A-B)$_y$-E-  (IV)

wherein (i) y is 0 to 30;

(ii) each A independently for each y is a divalent group selected from the group consisting of aliphatic group and haloaliphatic group;

(iii) each B independently for each y is a divalent group selected from the group consisting of —O—; —C(O)O—; —OC(O)O—; —C(O)N($R_1$)— where $R_1$ is H or alkyl; —NH—C(O)O—; —N($R_2$)C(O)N($R_2$)— where each $R_2$ is independently selected from H or alkyl;

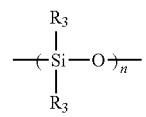

where n is 1 to 5; and each $R_3$ independently for each n is selected from methyl, ethyl, or phenyl; and —Si($R_4$)($R_4$)— where each $R_4$ is independently selected from methyl, ethyl, or phenyl; and (iv) E is a divalent group selected from the group consisting of aliphatic group and haloaliphatic group, provided that at least one of Mesogen-1, Mesogen-2, or Mesogen-3, include at least four cyclic groups, and provided that -$L^1$- and -$L^2$- each independently comprise an average chain length of at least 20 bonds.

Clause 2: The mesogen-containing compound of clause 1, wherein independently for each of Formula (II) and Formula (III)

Q1, Q2, and Q3, for each occurrence, are independently a divalent group selected from the group consisting of unsubstituted or substituted cycloalkyl; unsubstituted or substituted phenyl; unsubstituted or substituted naphthyl; and unsubstituted or substituted triptycenyl; wherein the cycloalkyl substituents, phenyl substituents, naphthyl substituents, and triptycenyl substituents are each independently selected from cyano or —(S1)d-P, where S1, d, and P are each as defined with regard to Formula (II).

Clause 3: The mesogen-containing compound of clauses 1 or 2, wherein independently for each of Formula (II) and Formula (III)

Q1, Q2, and Q3 for each occurrence, are independently a divalent group selected from the group consisting of unsubstituted or substituted 1,4-cyclohexyl; unsubstituted or substituted 1,4-phenyl; unsubstituted or substituted 1,5-naphthyl; unsubstituted or substituted 2,6-naphthyl; unsubstituted or substituted 1,8-naphthyl; and unsubstituted or substituted 1,4-triptycenyl, wherein the 1,4-cycloalkyl substituents, 1,4-phenyl substituents, 1,5-naphthyl substituents, 2,6-naphthyl substituents, 1,8-naphthyl substituents, and 1,4-triptycenyl substituents are each independently selected from cyano or —(S1)d-P, where S1, d, and P are each as defined with regard to Formula (II).

Clause 4: The mesogen-containing compound of any one of clauses 1 to 3. wherein for Formula (II)

P is selected from hydrogen, alkyl, alkoxy, acrylate, or methacrylate;

for Formula (IV)
(i) y is 1 to 30;
(ii) each A independently for each y is a divalent group selected from the group consisting of alkyl and haloalkyl;
(iii) each B independently for each y is a divalent group selected from the group consisting of —O—; —C(O)O—; —OC(O)O—; —C(O)N($R_1$)— where $R_1$ is H or alkyl; —NH—C(O)O—; —N($R_2$)C(O)N($R_2$)— where each $R_2$ is independently selected from H or alkyl;

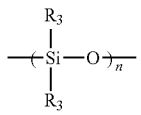

where n is 1 to 5, and each $R_3$ independently for each n is selected from methyl or phenyl; and —Si($R_4$)($R_4$)— where each $R_4$ is independently selected from methyl or phenyl; and
(iv) E is a divalent group selected from the group consisting of alkyl groups and haloalkyl groups.

Clause 5: The mesogen-containing compound of any one of clauses 1 to 4, wherein
Mesogen-1 is represented by Formula (II),
wherein P of Formula (II) is selected from acrylate, methacrylate, trihalomethacrylate, cyanoacrylate, oxirane, hydroxyl, primary amino, carboxylic acid, or carboxylic acid ester; and
Mesogen-3 is represented by the following Formula (V),

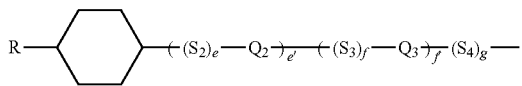
(V)

wherein R is selected from hydrogen, halogen, alkyl, haloalkyl, alkoxy, or haloalkoxy, and
$S_2$, $S_3$, $S_4$, $Q_2$, $Q_3$, e', f', e, and f are each independently as defined with regard to Formula (II).

Clause 6: The mesogen-containing compound of any one of clauses 1 to 5, wherein
Mesogen-1 and Mesogen-3 are each independently represented by the following Formula (V),

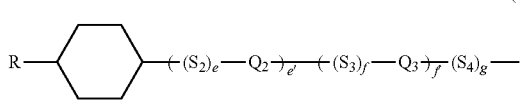
(V)

wherein R is selected from hydrogen, halogen, alkyl, haloalkyl, alkoxy, or haloalkoxy, and
$S_2$, $S_3$, $S_4$, $Q_2$, $Q_3$, e', f', e, and f are each independently as defined with regard to Formula (II).

Clause 7: The mesogen-containing compound of any one of clauses 1 to 6, wherein Mesogen-1 and Mesogen-3 are the same.

Clause 8: The mesogen-containing compound of any one of clauses 1 to 7, wherein -$L^1$- and -$L^2$- each independently comprise an average chain length of at least 25 bonds, or at least 30 bonds.

Clause 9: The mesogen-containing compound of any one of clauses 1 to 8, wherein -$L^1$- and -$L^2$- each independently comprise an average chain length of 20 to 200 bonds, or 25 to 150 bonds, or 30 to 100 bonds.

Clause 10: The mesogen-containing compound of any one of clauses 1 to 9, wherein -$L^1$- and -$L^2$- of Formula (I) are each independently selected from Formula L(1) through Formula L(22), including combinations of two or more thereof, as described previously herein.

Clause 11: A liquid crystal composition comprising the mesogen-containing compound of any one of clauses 1-10.

Clause 12: The liquid crystal composition of clause 11, further comprising at least one of a photochromic compound, a dichroic compound, or a photochromic-dichroic compound.

Clause 13: The liquid crystal composition of clause 12, wherein the photochromic-dichroic compound comprises at least one photochromic moiety, and said photochromic compound and each photochromic moiety of said photochromic-dichroic compound are in each case independently selected from indeno-fused naphthopyrans, naphtho[1,2-b]pyrans, naphtho[2,1-b]pyrans, spirofluoreno[1,2-b]pyrans, phenanthropyrans, quinolinopyrans, fluoroanthenopyrans, spiropyrans, benzoxazines, naphthoxazines, spiro(indoline) naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, non-thermally reversible photochromic compounds, or mixtures thereof.

Clause 14: An optical element comprising:
a substrate; and
a layer on at least a portion of a surface of the substrate, wherein the layer comprises the mesogen-containing compound of any one of clauses 1-10.

Clause 15: The optical element of clause 14, further comprising an alignment layer interposed between said substrate and said layer, wherein said alignment layer is at least partially alignable by exposure to at least one of a magnetic field, an electric field, linearly polarized radiation, shear force, or combinations of two or more thereof.

Clause 16: The optical element of clauses 14 or 15, wherein the optical element is selected from a display element, a window, a mirror, a liquid crystal cell element, or an ophthalmic element.

Clause 17: The optical element of clause 16, wherein the ophthalmic element is selected from a corrective lens, a non-corrective lens, a contact lens, an intra-ocular lens, a magnifying lens, a protective lens, or a visor.

The present invention has been described with reference to specific details of particular embodiments thereof. It is not intended that such details be regarded as limitations upon the scope of the invention except insofar as to the extent that they are included in the accompanying claims.

What is claimed is:

1. A mesogen-containing compound represented by the following Formula (I), (Mesogen-1)-$L^1$-(Mesogen-2)-$L^2$-(Mesogen-3)    (I)

wherein
(A) Mesogen-1 and Mesogen-3 are each independently represented by the following Formula (II), (II)

P—$(S_1)_d$—$Q_1$—$(S_2)_e$$_{e'}$—$Q_2$$_{e''}$—$(S_3)_f$—$Q_3$$_{f''}$$(S_4)_g$— wherein for Formula (II),

P is selected from hydrogen, halogen, alkyl, haloalkyl, alkoxy, haloalkoxy, acrylate, methacrylate, trihalomethacrylate, cyanoacrylate, acrylamido, methacrylamido, oxirane, hydroxyl, primary amino, carboxylic acid, or carboxylic acid ester;

(B) Mesogen-2 is represented by the following Formula (III),

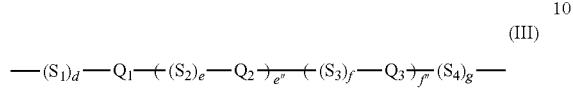

(III)

wherein independently for each of Formula (II) and Formula (III)

$S_1$, $S_2$, $S_3$, and $S_4$, for each occurrence, are independently selected from a spacer unit chosen from —$CH_2$—; —O—; —C(O)—; —N=N—; —CH=CH—; —C≡C—; —CH=N—; —$CF_2$—; or —NH—, provided that when two spacer units comprising heteroatoms are linked together the spacer units are linked so that heteroatoms are not directly linked to each other;

d is 0 to 20;

e, f, and g, for each occurrence, are independently 0 to 3;

$Q_1$, $Q_2$, and $Q_3$, for each occurrence, are independently a divalent group selected from the group consisting of unsubstituted or substituted cycloaliphatic group; unsubstituted or substituted heterocycloaliphatic group; unsubstituted or substituted aryl; and unsubstituted or substituted heteroaryl; wherein the cycloaliphatic group substituents, heterocycloaliphatic group substituents, aryl substituents, and heteroaryl substituents are each independently selected from cyano or —$(S_1)_d$—P, where $S_1$, d, and P are each as defined with regard to Formula (II); and e″ and f″, for each occurrence, are independently from 0 to 6, provided the sum of e″ and f″ is at least 1; and (C) -$L^1$- and -$L^2$- are each independently represented by the following Formula (IV), -(A-B)$_y$-E-    (IV)

wherein (i) y is 0 to 30;

(ii) each A independently for each y is a divalent group selected from the group consisting of aliphatic group and haloaliphatic group;

(iii) each B independently for each y is a divalent group selected from the group consisting of —O—; —C(O)O—; —OC(O)O—; —C(O)N($R_1$)— where $R_1$ is H or alkyl;

—NH—C(O)O—; —N($R_2$)C(O)N($R_2$)— where each $R_2$ is independently selected from H or alkyl;

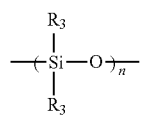

where n is 1 to 5, and each $R_3$ independently for each n is selected from methyl, ethyl, or phenyl; and —Si($R_4$)($R_4$)— where each $R_4$ is independently selected from methyl, ethyl, or phenyl; and (iv) E is a divalent group selected from the group consisting of aliphatic group and haloaliphatic group, provided that at least one of Mesogen-1, Mesogen-2, or Mesogen-3, include at least four cyclic groups, and provided that -$L^1$- and -$L^2$- each independently comprise an average chain length of at least 20 bonds.

2. The mesogen-containing compound of claim 1, wherein independently for each of Formula (II) and Formula (III), $Q_1$, $Q_2$, and $Q_3$, for each occurrence, are independently a divalent group selected from the group consisting of unsubstituted or substituted cycloalkyl; unsubstituted or substituted phenyl; unsubstituted or substituted naphthyl; and unsubstituted or substituted triptycenyl; wherein the cycloalkyl substituents, phenyl substituents, naphthyl substituents, and triptycenyl substituents, are each independently selected from cyano or —$(S_1)_d$—P, where $S_1$, d, and P are each as defined with regard to Formula (II).

3. The mesogen-containing compound of claim 1, wherein independently for each of Formula (II) and Formula (III), $Q_1$, $Q_2$, and $Q_3$ for each occurrence, are independently a divalent group selected from the group consisting of unsubstituted or substituted 1,4-cyclohexyl; unsubstituted or substituted 1,4-phenyl; unsubstituted or substituted 1,5-naphthyl; unsubstituted or substituted 2,6-naphthyl; unsubstituted or substituted 1,8-naphthyl; and unsubstituted or substituted 1,4-triptycenyl, wherein the 1,4-cyclohexyl substituents, 1,4-phenyl substituents, 1,5-naphthyl substituents, 2,6-naphthyl substituents, 1,8-naphthyl substituents, and 1,4-triptycenyl substituents are each independently selected from cyano or —$(S_1)_d$—P, where $S_1$, d, and P are each as defined with regard to Formula (II).

4. The mesogen-containing compound of claim 1, wherein for Formula (II)

P is selected from hydrogen, alkyl, alkoxy, acrylate, or methacrylate;

for Formula (IV)

(i) y is 1 to 30;

(ii) each A independently for each y is a divalent group selected from the group consisting of alkyl and haloalkyl;

(iii) each B independently for each y is a divalent group selected from the group consisting of —O—; —C(O)O—; —OC(O)O—; —C(O)N($R_1$)— where $R_1$ is H or alkyl;

—NH—C(O)O—; —N($R_2$)C(O)N($R_2$)— where each $R_2$ is independently selected from H or alkyl;

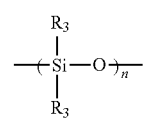

where n is 1 to 5, and each $R_3$ independently for each n is selected from methyl or phenyl; and —Si($R_4$)($R_4$)— where each $R_4$ is independently selected from methyl or phenyl; and (iv) E is a divalent group selected from the group consisting of alkyl groups and haloalkyl groups.

5. The mesogen-containing compound of claim 1, wherein
Mesogen-1 is represented by Formula (II),
wherein P of Formula (II) is selected from acrylate, methacrylate, trihalomethacrylate, cyanoacrylate, oxirane, hydroxyl, primary amino, carboxylic acid, or carboxylic acid ester; and
Mesogen-3 is represented by the following Formula (V),

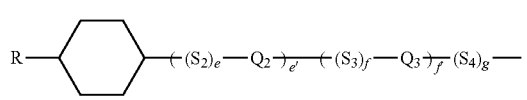

(V)

wherein R is selected from hydrogen, halogen, alkyl, haloalkyl, alkoxy, or haloalkoxy, and
$S_2$, $S_3$, $S_4$, $Q_2$, $Q_3$, e', f', e, and f are each independently as defined with regard to Formula (II).

6. The mesogen-containing compound of claim 1, wherein
Mesogen-1 and Mesogen-3 are each independently represented by the following Formula (V),

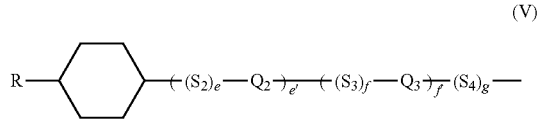

(V)

wherein R is selected from hydrogen, halogen, alkyl, haloalkyl, alkoxy, or haloalkoxy, and
$S_2$, $S_3$, $S_4$, $Q_2$, $Q_3$, e', f', e, and f are each independently as defined with regard to Formula (II).

7. The mesogen-containing compound of claim 1, wherein Mesogen-1 and Mesogen-3 are the same.

8. The mesogen-containing compound of claim 1, wherein -$L^1$- and -$L^2$- each independently comprise an average chain length of at least 25 bonds.

9. A liquid crystal composition comprising the mesogen-containing compound of claim 1.

10. The liquid crystal composition of claim 9, further comprising at least one of a photochromic compound, a dichroic compound, or a photochromic-dichroic compound.

11. The liquid crystal composition of claim 10, wherein said photochromic-dichroic compound comprises at least one photochromic moiety, and said photochromic compound and each photochromic moiety of said photochromic-dichroic compound are in each case independently selected from indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline) naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, non-thermally reversible photochromic compounds, and mixtures thereof.

12. An optical element comprising:
a substrate; and
a layer on at least a portion of a surface of said substrate, wherein said layer comprises the mesogen-containing compound of claim 1.

13. The optical element of claim 12, further comprising an alignment layer interposed between said substrate and said layer, wherein said alignment layer is at least partially alignable by exposure to at least one of a magnetic field, an electric field, linearly polarized radiation, shear force, or combinations of two or more thereof.

14. The optical element of claim 12, wherein said optical element is selected from a display element, a window, a mirror, a liquid crystal cell element, or an ophthalmic element.

15. The optical element of claim 14, wherein said ophthalmic element is selected from a corrective lens, a non-corrective lens, a contact lens, an intra-ocular lens, a magnifying lens, a protective lens, or a visor.

* * * * *